US012629503B2

(12) United States Patent
Tong et al.

(10) Patent No.: US 12,629,503 B2
(45) Date of Patent: *May 19, 2026

(54) DRUG DELIVERY METHODS AND SYSTEMS

(71) Applicant: MORNINGSIDE VENTURE INVESTMENTS LIMITED, Monaco (MC)

(72) Inventors: Ling-Kang Tong, Hayward, CA (US); Daniela Tamar Buchman, Mountain View, CA (US); Jackie Joe Hancock, Berkeley, CA (US); Nicholas Terzulli, Oakland, CA (US)

(73) Assignee: MORNINGSIDE VENTURE INVESTMENTS LIMITED (MC)

( * ) Notice: Subject to any disclaimer, the term of this patent is extended or adjusted under 35 U.S.C. 154(b) by 32 days.

This patent is subject to a terminal disclaimer.

(21) Appl. No.: 18/665,410

(22) Filed: May 15, 2024

(65) Prior Publication Data

US 2024/0416095 A1     Dec. 19, 2024

Related U.S. Application Data

(63) Continuation of application No. 18/178,442, filed on Mar. 3, 2023, now Pat. No. 12,017,029, which is a
(Continued)

(51) Int. Cl.
*A61M 35/00* (2006.01)
*A61M 5/142* (2006.01)

(52) U.S. Cl.
CPC ........ *A61M 35/10* (2019.05); *A61M 5/14248* (2013.01); *A61M 2005/14268* (2013.01);
(Continued)

(58) Field of Classification Search
CPC .... A61M 2005/14268; A61M 5/14248; A61M 5/1413
See application file for complete search history.

(56) References Cited

U.S. PATENT DOCUMENTS

| | | | |
|---|---|---|---|
| 2,183,482 A | 12/1939 | Kurkjian |
| 3,279,653 A | 10/1966 | Pfleger |
| | (Continued) | |

FOREIGN PATENT DOCUMENTS

| | | | |
|---|---|---|---|
| AU | 662877 B3 | 9/1995 |
| BE | 899037 A | 6/1984 |
| | (Continued) | |

OTHER PUBLICATIONS

Abood et al.; Structure-activity studies of carbamate and other esters: agonists and antagonists to nicotine; Pharmacology Biochemistry and Behavior; 30(2); pp. 403-408; Jun. 1988.
(Continued)

*Primary Examiner* — Andrew J Mensh
*Assistant Examiner* — Arjuna P Chatrathi
(74) *Attorney, Agent, or Firm* — Shay Glenn LLP

(57) ABSTRACT

A two-part bioactive agent delivery system includes a disposable part, a reusable part, and a solvent removal element. The disposable part includes an agent reservoir, a transdermal patch communicating with the agent reservoir and adapted to transdermally deliver the bioactive agent to a user. The transdermal patch has a bottom surface adapted to contact skin of the user, a top surface opposite the bottom surface, and a gas permeable membrane disposed over the top surface of the transdermal patch. The reusable part includes a power source and control electronics that are adapted to deliver bioactive agent dissolved in a solvent from the agent reservoir to the transdermal patch. The solvent removal element includes a gap disposed between
(Continued)

the disposable part and the reusable part to create a flow path for gaseous solvent to flow from the gas permeable membrane to ambient air around the bioactive agent delivery system.

19 Claims, 14 Drawing Sheets

Related U.S. Application Data continuation of application No. 17/057,318, filed as application No. PCT/US2019/034432 on May 29, 2019, now Pat. No. 11,596,779.

(60) Provisional application No. 62/677,494, filed on May 29, 2018.

(52) U.S. Cl.
CPC . *A61M 2205/0272* (2013.01); *A61M 2205/14* (2013.01); *A61M 2205/8206* (2013.01)

(56)                    References Cited

U.S. PATENT DOCUMENTS

| | | |
|---|---|---|
| 3,845,217 A | 10/1974 | Ferno et al. |
| 4,313,439 A | 2/1982 | Babb et al. |
| 4,321,387 A | 3/1982 | Chavdarian et al. |
| 4,327,725 A | 5/1982 | Cortese et al. |
| 4,332,945 A | 6/1982 | Edwards |
| 4,379,454 A | 4/1983 | Campbell et al. |
| 4,545,990 A | 10/1985 | Le Foyer de Costil et al. |
| 4,579,858 A | 4/1986 | Ferno et al. |
| 4,590,278 A | 5/1986 | Edwards |
| 4,597,961 A | 7/1986 | Etscorn |
| 4,708,716 A | 11/1987 | Sibalis |
| 4,772,263 A | 9/1988 | Dorman et al. |
| 4,806,356 A | 2/1989 | Shaw |
| 4,853,854 A | 8/1989 | Behar et al. |
| 4,885,154 A | 12/1989 | Cormier et al. |
| 4,908,213 A | 3/1990 | Govil et al. |
| 4,917,676 A | 4/1990 | Heiber et al. |
| 4,917,895 A | 4/1990 | Lee et al. |
| 4,920,989 A | 5/1990 | Rose et al. |
| 4,952,928 A | 8/1990 | Carroll et al. |
| 4,953,572 A | 9/1990 | Rose et al. |
| 4,992,445 A | 2/1991 | Lawter et al. |
| 4,994,278 A | 2/1991 | Sablotsky et al. |
| 5,000,956 A | 3/1991 | Amkraut et al. |
| 5,001,139 A | 3/1991 | Lawter et al. |
| 5,013,293 A | 5/1991 | Sibalis |
| 5,023,252 A | 6/1991 | Hseih |
| 5,049,387 A | 9/1991 | Amkraut |
| 5,069,904 A | 12/1991 | Masterson |
| 5,073,380 A | 12/1991 | Babu et al. |
| 5,097,834 A | 3/1992 | Skrabal |
| 5,120,545 A | 6/1992 | Ledger et al. |
| 5,130,139 A | 7/1992 | Cormier et al. |
| 5,149,538 A | 9/1992 | Granger et al. |
| 5,149,719 A | 9/1992 | Ferber et al. |
| 5,212,188 A | 5/1993 | Caldwell et al. |
| 5,221,254 A | 6/1993 | Phipps |
| 5,227,391 A | 7/1993 | Caldwell et al. |
| 5,232,704 A | 8/1993 | Franz et al. |
| 5,232,933 A | 8/1993 | Lippiello et al. |
| 5,236,714 A | 8/1993 | Lee et al. |
| 5,242,934 A | 9/1993 | Lippiello et al. |
| 5,242,935 A | 9/1993 | Lippiello et al. |
| 5,242,941 A | 9/1993 | Lewy et al. |
| 5,248,690 A | 9/1993 | Caldwel et al. |
| 5,252,604 A | 10/1993 | Nagy et al. |
| 5,262,165 A | 11/1993 | Govil et al. |
| 5,273,755 A | 12/1993 | Venkatraman et al. |
| 5,273,756 A | 12/1993 | Fallon et al. |
| 5,304,739 A | 4/1994 | Klug et al. |
| 5,310,404 A | 5/1994 | Gyory et al. |
| 5,352,456 A | 10/1994 | Fallon et al. |
| 5,364,630 A | 11/1994 | Osborne et al. |
| 5,370,635 A | 12/1994 | Strausak et al. |
| 5,388,571 A | 2/1995 | Roberts et al. |
| 5,389,679 A | 2/1995 | Alliger |
| 5,393,526 A | 2/1995 | Castro |
| 5,405,614 A | 4/1995 | D'Angelo et al. |
| 5,415,629 A | 5/1995 | Henley |
| 5,445,609 A | 8/1995 | Lattin et al. |
| 5,451,407 A | 9/1995 | Cormier et al. |
| 5,464,387 A | 11/1995 | Haak et al. |
| 5,472,946 A | 12/1995 | Peck et al. |
| 5,501,697 A | 3/1996 | Fisher |
| 5,505,958 A | 4/1996 | Bello et al. |
| 5,512,306 A | 4/1996 | Carlsson et al. |
| 5,516,793 A | 5/1996 | Duffy |
| 5,525,351 A | 6/1996 | Dam |
| 5,545,407 A | 8/1996 | Hall et al. |
| 5,562,607 A | 10/1996 | Gyory |
| 5,596,994 A | 1/1997 | Bro |
| 5,601,839 A | 2/1997 | Quan et al. |
| 5,616,332 A | 4/1997 | Herstein |
| 5,618,557 A | 4/1997 | Wille et al. |
| 5,653,682 A | 8/1997 | Sibalis |
| 5,656,255 A | 8/1997 | Jones |
| 5,662,920 A | 9/1997 | Santus |
| 5,686,100 A | 11/1997 | Wille et al. |
| 5,688,232 A | 11/1997 | Flower |
| 5,697,896 A | 12/1997 | McNichols et al. |
| 5,716,987 A | 2/1998 | Wille |
| 5,722,418 A | 3/1998 | Bro |
| 5,733,259 A | 3/1998 | Valcke et al. |
| 5,785,688 A | 7/1998 | Joshi et al. |
| 5,797,867 A | 8/1998 | Guerrera et al. |
| 5,820,875 A | 10/1998 | Fallon et al. |
| 5,833,466 A | 11/1998 | Borg |
| 5,843,979 A | 12/1998 | Wille et al. |
| 5,846,559 A | 12/1998 | Hopp |
| 5,865,786 A | 2/1999 | Sibalis et al. |
| 5,876,368 A | 3/1999 | Flower |
| 5,879,292 A | 3/1999 | Sternberg et al. |
| 5,879,322 A | 3/1999 | Lattin et al. |
| 5,882,676 A | 3/1999 | Lee et al. |
| 5,908,301 A | 6/1999 | Lutz |
| 5,919,156 A | 7/1999 | Stropkay et al. |
| 5,932,240 A | 8/1999 | D'Angelo et al. |
| 5,945,123 A | 8/1999 | Hermelin |
| 5,967,789 A | 10/1999 | Segel et al. |
| 5,972,389 A | 10/1999 | Shell et al. |
| 5,993,435 A | 11/1999 | Haak et al. |
| 5,997,501 A | 12/1999 | Gross et al. |
| 6,018,679 A | 1/2000 | Dinh et al. |
| 6,019,997 A | 2/2000 | Scholz et al. |
| 6,024,981 A | 2/2000 | Khankari et al. |
| 6,034,079 A | 3/2000 | Sanberg et al. |
| 6,059,736 A | 5/2000 | Tapper |
| 6,059,753 A | 5/2000 | Faust et al. |
| 6,068,853 A | 5/2000 | Giannos et al. |
| 6,081,734 A | 6/2000 | Batz |
| 6,090,404 A | 7/2000 | Meconi et al. |
| 6,093,419 A | 7/2000 | Rolf |
| 6,120,803 A | 9/2000 | Wong et al. |
| 6,129,702 A | 10/2000 | Woias et al. |
| 6,162,214 A | 12/2000 | Mueller et al. |
| 6,165,155 A | 12/2000 | Jacobsen et al. |
| 6,211,194 B1 | 4/2001 | Westman et al. |
| 6,211,296 B1 | 4/2001 | Frate et al. |
| 6,221,394 B1 | 4/2001 | Gilbert et al. |
| 6,238,689 B1 | 5/2001 | Rhodes et al. |
| 6,274,606 B1 | 8/2001 | Caldwell et al. |
| 6,310,102 B1 | 10/2001 | Dull et al. |
| 6,365,182 B1 | 4/2002 | Khankari et al. |
| 6,368,625 B1 | 4/2002 | Siebert et al. |
| 6,374,136 B1 | 4/2002 | Murdock |
| 6,416,471 B1 | 7/2002 | Kumar et al. |
| 6,417,359 B1 | 7/2002 | Crooks et al. |
| 6,423,747 B1 | 7/2002 | Lanzendörfer et al. |

(56)                References Cited

U.S. PATENT DOCUMENTS

| | | |
|---|---|---|
| 6,436,078 B1 | 8/2002 | Svedman |
| 6,437,004 B1 | 8/2002 | Perricone |
| 6,454,708 B1 | 9/2002 | Ferguson et al. |
| 6,488,959 B2 | 12/2002 | Stanley et al. |
| 6,492,399 B1 | 12/2002 | Dull et al. |
| 6,539,250 B1 | 3/2003 | Bettinger |
| 6,546,281 B1 | 4/2003 | Zhang et al. |
| 6,567,785 B2 | 5/2003 | Clendenon |
| 6,569,449 B1 | 5/2003 | Stinchcomb et al. |
| 6,569,866 B2 | 5/2003 | Simon |
| 6,576,269 B1 | 6/2003 | Korneyev |
| 6,579,865 B2 | 6/2003 | Mak et al. |
| 6,589,229 B1 | 7/2003 | Connelly et al. |
| 6,595,956 B1 | 7/2003 | Gross et al. |
| 6,638,528 B1 | 10/2003 | Kanios |
| 6,638,543 B2 | 10/2003 | Kang et al. |
| 6,660,295 B2 | 12/2003 | Watanabe et al. |
| 6,689,380 B1 | 2/2004 | Marchitto et al. |
| 6,723,086 B2 | 4/2004 | Bassuk et al. |
| 6,723,340 B2 | 4/2004 | Gusler et al. |
| 6,746,688 B1 | 6/2004 | Kushnir et al. |
| 6,791,003 B1 | 9/2004 | Choi et al. |
| 6,799,576 B2 | 10/2004 | Farr |
| 6,849,645 B2 | 2/2005 | Majeed et al. |
| 6,861,066 B2 | 3/2005 | Van de Casteele |
| 6,867,342 B2 | 3/2005 | Johnston et al. |
| 6,887,202 B2 | 5/2005 | Currie et al. |
| 6,893,655 B2 | 5/2005 | Flanigan et al. |
| 6,900,202 B2 | 5/2005 | Imoto et al. |
| 6,911,475 B1 | 6/2005 | Villafane et al. |
| 6,998,176 B2 | 2/2006 | Morita et al. |
| 7,011,843 B2 | 3/2006 | Becher et al. |
| 7,011,849 B2 | 3/2006 | Storm et al. |
| 7,019,622 B2 | 3/2006 | Orr et al. |
| 7,064,143 B1 | 6/2006 | Gurley et al. |
| 7,182,955 B2 | 2/2007 | Hart et al. |
| 7,196,619 B2 | 3/2007 | Perlman et al. |
| 7,229,641 B2 | 6/2007 | Cherukuri |
| 7,282,217 B1 | 10/2007 | Grimshaw et al. |
| 7,332,182 B2 | 2/2008 | Sackler |
| 7,376,700 B1 | 5/2008 | Clark et al. |
| 7,384,651 B2 | 6/2008 | Hille et al. |
| 7,384,653 B2 | 6/2008 | Wright et al. |
| 7,579,019 B2 | 8/2009 | Tapolsky et al. |
| 7,598,275 B2 | 10/2009 | Cooke et al. |
| 7,718,677 B2 | 5/2010 | Quik et al. |
| 7,780,981 B2 | 8/2010 | DiPierro et al. |
| 7,931,563 B2 | 4/2011 | Shaw et al. |
| 7,988,660 B2 | 8/2011 | Byland et al. |
| 8,003,080 B2 | 8/2011 | Rabinowitz et al. |
| 8,021,334 B2 | 9/2011 | Shekalim |
| 8,137,314 B2 | 3/2012 | Mounce et al. |
| 8,140,143 B2 | 3/2012 | Picard et al. |
| 8,192,756 B2 | 6/2012 | Berner et al. |
| 8,246,581 B2 | 8/2012 | Adams et al. |
| 8,252,321 B2 | 8/2012 | DiPierro et al. |
| 8,262,394 B2 | 9/2012 | Walker et al. |
| 8,268,475 B2 | 9/2012 | Tucholski |
| 8,285,328 B2 | 10/2012 | Caffey et al. |
| 8,303,500 B2 | 11/2012 | Raheman |
| 8,309,568 B2 | 11/2012 | Stinchcomb et al. |
| 8,372,040 B2 | 2/2013 | Huang et al. |
| 8,414,532 B2 | 4/2013 | Brandt et al. |
| 8,440,220 B2 | 5/2013 | Gale et al. |
| 8,440,221 B2 | 5/2013 | Zumbrunn et al. |
| 8,441,411 B2 | 5/2013 | Tucholski et al. |
| 8,445,010 B2 | 5/2013 | Anderson et al. |
| 8,449,471 B2 | 5/2013 | Tran |
| 8,517,988 B2 | 8/2013 | Smith |
| 8,545,445 B2 | 10/2013 | Kamen et al. |
| 8,574,188 B2 | 11/2013 | Potter et al. |
| 8,586,079 B2 | 11/2013 | Hansted et al. |
| 8,589,174 B2 | 11/2013 | Nelson et al. |
| 8,614,278 B2 | 12/2013 | Loubert et al. |
| 8,632,497 B2 | 1/2014 | Yodfat et al. |
| 8,666,781 B2 | 3/2014 | Hanina et al. |
| 8,673,346 B2 | 3/2014 | Zumbrunn et al. |
| 8,684,922 B2 | 4/2014 | Tran |
| 8,688,189 B2 | 4/2014 | Shennib |
| 8,690,827 B2 | 4/2014 | Edwards et al. |
| 8,690,865 B2 | 4/2014 | Prausnitz et al. |
| 8,696,637 B2 | 4/2014 | Ross |
| 8,703,175 B2 | 4/2014 | Kanios et al. |
| 8,703,177 B2 | 4/2014 | Finn et al. |
| 8,722,233 B2 | 5/2014 | Tucholski |
| 8,727,745 B2 | 5/2014 | Rush et al. |
| 8,741,336 B2 | 6/2014 | DiPierro et al. |
| 8,747,348 B2 | 6/2014 | Yodfat et al. |
| 8,753,315 B2 | 6/2014 | Alferness et al. |
| 8,773,257 B2 | 7/2014 | Yodfat et al. |
| 8,814,822 B2 | 8/2014 | Yodfat et al. |
| 8,862,223 B2 | 10/2014 | Yanaki |
| 8,864,727 B2 | 10/2014 | Lee |
| 8,865,207 B2 | 10/2014 | Kanios et al. |
| 8,872,663 B2 | 10/2014 | Forster |
| 8,876,802 B2 | 11/2014 | Grigorov |
| 8,956,644 B2 | 2/2015 | Yum et al. |
| 8,962,014 B2 | 2/2015 | Prinz et al. |
| 8,986,253 B2 | 3/2015 | DiPerna |
| 8,999,356 B1 | 4/2015 | Ramirez et al. |
| 8,999,372 B2 | 4/2015 | Davidson et al. |
| 9,023,392 B2 | 5/2015 | Koo et al. |
| 9,044,582 B2 | 6/2015 | Chang et al. |
| 9,050,348 B2 | 6/2015 | Kydonieus et al. |
| 9,078,833 B2 | 7/2015 | Audett |
| 9,111,085 B1 | 8/2015 | Darmour et al. |
| 9,114,240 B2 | 8/2015 | Horstmann et al. |
| 9,155,712 B2 | 10/2015 | Kanios et al. |
| 9,233,203 B2 | 1/2016 | Moberg et al. |
| 9,238,001 B2 | 1/2016 | Weyer et al. |
| 9,238,108 B2 | 1/2016 | Edwards et al. |
| 9,248,104 B2 | 2/2016 | Valia et al. |
| 9,289,397 B2 | 3/2016 | Wright |
| 9,308,202 B2 | 4/2016 | Hille et al. |
| 9,314,527 B2 | 4/2016 | Cottrell et al. |
| 9,373,269 B2 | 6/2016 | Bergman et al. |
| 9,380,698 B1 | 6/2016 | Li et al. |
| RE46,217 E | 11/2016 | Huang et al. |
| 9,513,666 B2 | 12/2016 | Li et al. |
| 9,549,903 B2 | 1/2017 | Hille et al. |
| 9,555,226 B2 | 1/2017 | Zumbrunn et al. |
| 9,555,227 B2 | 1/2017 | Dipierro |
| 9,555,277 B2 | 1/2017 | Yeh |
| 9,623,017 B2 | 4/2017 | Barbier et al. |
| 9,636,457 B2 | 5/2017 | Newberry et al. |
| 9,655,843 B2 | 5/2017 | Finn et al. |
| 9,656,441 B2 | 5/2017 | LeDonne et al. |
| 9,669,199 B2 | 6/2017 | DiPierro et al. |
| 9,687,186 B2 | 6/2017 | Goldstein et al. |
| 9,693,689 B2 | 7/2017 | Gannon et al. |
| 9,700,552 B2 | 7/2017 | Weimann |
| 9,717,698 B2 | 8/2017 | Horstmann et al. |
| 9,735,893 B1 | 8/2017 | Aleksov et al. |
| 9,782,082 B2 | 10/2017 | Gannon et al. |
| 9,795,681 B2 | 10/2017 | Abreu |
| 9,867,539 B2 | 1/2018 | Heikenfeld et al. |
| 9,895,320 B2 | 2/2018 | Ogino et al. |
| 9,949,935 B2 | 4/2018 | Murata |
| 9,974,492 B1 | 5/2018 | Dicks et al. |
| 9,993,203 B2 | 6/2018 | Mel et al. |
| 10,004,447 B2 | 6/2018 | Shen et al. |
| 10,034,841 B2 | 7/2018 | Müller et al. |
| 10,105,487 B2 | 10/2018 | DiPierro et al. |
| 10,143,687 B2 | 12/2018 | Azhir |
| 10,213,586 B2 | 2/2019 | Netzel et al. |
| 10,232,156 B2 | 3/2019 | Netzel et al. |
| 10,258,738 B2 | 4/2019 | Dipierro et al. |
| 10,258,778 B2 | 4/2019 | DiPierro et al. |
| 10,679,516 B2 | 6/2020 | Darmour et al. |
| 10,716,764 B2 | 7/2020 | Zumbrunn et al. |
| 11,285,306 B2 | 3/2022 | Johnson et al. |
| 11,400,266 B2 | 8/2022 | Netzel et al. |
| 11,471,424 B2 | 10/2022 | DiPierro |
| 11,596,779 B2 | 3/2023 | Tong et al. |

(56)  References Cited

U.S. PATENT DOCUMENTS

| | | |
|---|---|---|
| 12,011,560 B2 | 6/2024 | Netzel et al. |
| 12,017,029 B2 * | 6/2024 | Tong .................... A61M 35/10 |
| 2001/0022978 A1 | 9/2001 | Lacharriere et al. |
| 2001/0026788 A1 | 10/2001 | Piskorz |
| 2002/0002189 A1 | 1/2002 | Smith et al. |
| 2002/0034535 A1 | 3/2002 | Kleiner et al. |
| 2002/0106329 A1 | 8/2002 | Leslie |
| 2002/0127256 A1 | 9/2002 | Murad |
| 2002/0165170 A1 | 11/2002 | Wilson et al. |
| 2002/0169439 A1 | 11/2002 | Flaherty |
| 2002/0182238 A1 | 12/2002 | Creton |
| 2003/0004187 A1 | 1/2003 | Bedard et al. |
| 2003/0065294 A1 | 4/2003 | Pickup et al. |
| 2003/0065924 A1 | 4/2003 | Wuidart et al. |
| 2003/0083645 A1 | 5/2003 | Angel et al. |
| 2003/0087937 A1 | 5/2003 | Lindberg |
| 2003/0119879 A1 | 6/2003 | Landh et al. |
| 2003/0138464 A1 | 7/2003 | Zhang et al. |
| 2003/0159702 A1 | 8/2003 | Lindell et al. |
| 2004/0019321 A1 | 1/2004 | Sage et al. |
| 2004/0034068 A1 | 2/2004 | Warchol et al. |
| 2004/0037879 A1 | 2/2004 | Adusumilli et al. |
| 2004/0052843 A1 | 3/2004 | Lerner et al. |
| 2004/0062802 A1 | 4/2004 | Hermelin |
| 2004/0138074 A1 | 7/2004 | Ahmad et al. |
| 2004/0166159 A1 | 8/2004 | Han et al. |
| 2004/0191322 A1 | 9/2004 | Hansson |
| 2004/0194793 A1 | 10/2004 | Lindell et al. |
| 2004/0219192 A1 | 11/2004 | Horstmann et al. |
| 2004/0229908 A1 | 11/2004 | Nelson |
| 2004/0241218 A1 | 12/2004 | Tavares et al. |
| 2004/0253249 A1 | 12/2004 | Rudnic et al. |
| 2004/0259816 A1 | 12/2004 | Pandol et al. |
| 2005/0002806 A1 | 1/2005 | Fuechslin et al. |
| 2005/0014779 A1 | 1/2005 | Papke |
| 2005/0021092 A1 | 1/2005 | Yun et al. |
| 2005/0034842 A1 | 2/2005 | Huber et al. |
| 2005/0048020 A1 | 3/2005 | Wille |
| 2005/0053665 A1 | 3/2005 | Ek et al. |
| 2005/0113452 A1 | 5/2005 | Flashner Barak et al. |
| 2005/0141346 A1 | 6/2005 | Rawls et al. |
| 2005/0151110 A1 | 7/2005 | Minor et al. |
| 2005/0159419 A1 | 7/2005 | Stephenson et al. |
| 2005/0197625 A1 | 9/2005 | Haueter et al. |
| 2005/0238704 A1 * | 10/2005 | Zumbrunn ........... A61K 9/7023 |
| | | 424/449 |
| 2005/0266032 A1 | 12/2005 | Srinivasan et al. |
| 2005/0276852 A1 | 12/2005 | Davis et al. |
| 2006/0024358 A1 | 2/2006 | Santini et al. |
| 2006/0036209 A1 | 2/2006 | Subramony et al. |
| 2006/0057202 A1 | 3/2006 | Antarkar et al. |
| 2006/0122577 A1 | 6/2006 | Poulsen et al. |
| 2006/0135911 A1 | 6/2006 | Mittur |
| 2006/0167039 A1 | 7/2006 | Nguyen et al. |
| 2006/0173439 A1 | 8/2006 | Thorne et al. |
| 2006/0184093 A1 | 8/2006 | Phipps et al. |
| 2006/0188859 A1 | 8/2006 | Yakobi |
| 2006/0204578 A1 | 9/2006 | Vergez et al. |
| 2006/0206054 A1 | 9/2006 | Shekalim |
| 2006/0271020 A1 * | 11/2006 | Huang .................... F04B 23/02 |
| | | 604/890.1 |
| 2007/0026054 A1 | 2/2007 | Theobald et al. |
| 2007/0042026 A1 | 2/2007 | Wille |
| 2007/0065365 A1 | 3/2007 | Kugelmann et al. |
| 2007/0086275 A1 | 4/2007 | Robinson et al. |
| 2007/0088338 A1 | 4/2007 | Ehwald et al. |
| 2007/0104787 A1 | 5/2007 | Dowty et al. |
| 2007/0149952 A1 | 6/2007 | Bland et al. |
| 2007/0154336 A1 | 7/2007 | Miyazaki et al. |
| 2007/0168501 A1 | 7/2007 | Cobb et al. |
| 2007/0179172 A1 | 8/2007 | Becker et al. |
| 2007/0191815 A1 | 8/2007 | DiPierro |
| 2007/0250018 A1 | 10/2007 | Adachi et al. |
| 2007/0255195 A1 | 11/2007 | Adachi |
| 2007/0256684 A1 | 11/2007 | Kelliher et al. |
| 2007/0260491 A1 | 11/2007 | Palmer et al. |
| 2007/0279217 A1 | 12/2007 | Venkatraman et al. |
| 2007/0299401 A1 | 12/2007 | Alferness et al. |
| 2008/0008747 A1 | 1/2008 | Royds |
| 2008/0015494 A1 | 1/2008 | Santini, Jr. et al. |
| 2008/0131494 A1 | 6/2008 | Reed et al. |
| 2008/0138294 A1 | 6/2008 | Gonda |
| 2008/0138398 A1 | 6/2008 | Gonda |
| 2008/0138399 A1 | 6/2008 | Gonda |
| 2008/0138423 A1 | 6/2008 | Gonda |
| 2008/0139907 A1 | 6/2008 | Rao et al. |
| 2008/0152592 A1 | 6/2008 | Rebec |
| 2008/0195946 A1 | 8/2008 | Peri-Glass |
| 2008/0201174 A1 | 8/2008 | Ramasubramanian et al. |
| 2008/0233178 A1 | 9/2008 | Reidenberg et al. |
| 2008/0274168 A1 | 11/2008 | Baker et al. |
| 2008/0319272 A1 | 12/2008 | Patangay et al. |
| 2009/0005009 A1 | 1/2009 | Marsili |
| 2009/0010998 A1 | 1/2009 | Marchitto et al. |
| 2009/0024004 A1 | 1/2009 | Yang |
| 2009/0028824 A1 | 1/2009 | Chiang et al. |
| 2009/0048563 A1 * | 2/2009 | Ethelfeld .......... A61M 5/14248 |
| | | 604/174 |
| 2009/0062754 A1 | 3/2009 | Tang |
| 2009/0118710 A1 | 5/2009 | Kortzeborn |
| 2009/0169631 A1 | 7/2009 | Zamloot et al. |
| 2009/0246265 A1 | 10/2009 | Stinchcomb et al. |
| 2009/0247985 A1 | 10/2009 | Melsheimer et al. |
| 2009/0259176 A1 | 10/2009 | Yairi |
| 2009/0299156 A1 | 12/2009 | Simpson et al. |
| 2010/0003653 A1 | 1/2010 | Brown |
| 2010/0010443 A1 | 1/2010 | Morgan et al. |
| 2010/0068250 A1 | 3/2010 | Anderson et al. |
| 2010/0114008 A1 | 5/2010 | Marchitto et al. |
| 2010/0130932 A1 | 5/2010 | Yodfat et al. |
| 2010/0145303 A1 | 6/2010 | Yodfat et al. |
| 2010/0179473 A1 | 7/2010 | Genosar |
| 2010/0196463 A1 | 8/2010 | Quik et al. |
| 2010/0198187 A1 | 8/2010 | Yodfat et al. |
| 2010/0211005 A1 | 8/2010 | Edwards et al. |
| 2010/0248198 A1 | 9/2010 | Seidman et al. |
| 2010/0273738 A1 | 10/2010 | Valcke et al. |
| 2010/0280432 A1 | 11/2010 | DiPierro et al. |
| 2011/0004072 A1 | 1/2011 | Fletcher et al. |
| 2011/0053129 A1 | 3/2011 | Basson et al. |
| 2011/0054285 A1 | 3/2011 | Searle et al. |
| 2011/0109439 A1 | 5/2011 | Borlenghi |
| 2011/0137255 A1 | 6/2011 | Nielsen et al. |
| 2011/0152635 A1 | 6/2011 | Morris et al. |
| 2011/0153360 A1 | 6/2011 | Hanina et al. |
| 2011/0160640 A1 | 6/2011 | Yanaki |
| 2011/0160655 A1 | 6/2011 | Hanson et al. |
| 2011/0212027 A1 | 9/2011 | Hoare et al. |
| 2011/0241446 A1 | 10/2011 | Tucholski |
| 2011/0245633 A1 | 10/2011 | Goldberg et al. |
| 2011/0245783 A1 | 10/2011 | Stinchcomb et al. |
| 2011/0250576 A1 | 10/2011 | Hester |
| 2011/0256517 A1 | 10/2011 | Swanson |
| 2011/0264028 A1 | 10/2011 | Ramdas et al. |
| 2011/0268809 A1 | 11/2011 | Brinkley et al. |
| 2011/0275987 A1 | 11/2011 | Caffey et al. |
| 2012/0046644 A1 | 2/2012 | Ziaie et al. |
| 2012/0078216 A1 | 3/2012 | Smith et al. |
| 2012/0123387 A1 | 5/2012 | Gonzalez et al. |
| 2012/0156138 A1 | 6/2012 | Smith |
| 2012/0171277 A1 | 7/2012 | Royds |
| 2012/0178065 A1 | 7/2012 | Naghavi et al. |
| 2012/0191043 A1 | 7/2012 | Yodfat et al. |
| 2012/0203573 A1 | 8/2012 | Mayer et al. |
| 2012/0209223 A1 | 8/2012 | Salman et al. |
| 2012/0221251 A1 | 8/2012 | Rosenberg et al. |
| 2012/0244503 A1 | 9/2012 | Neveldine |
| 2012/0302844 A1 | 11/2012 | Schnidrig et al. |
| 2012/0316896 A1 | 12/2012 | Rahman et al. |
| 2012/0329017 A1 | 12/2012 | Pham |
| 2013/0017259 A1 | 1/2013 | Azhir |
| 2013/0041258 A1 | 2/2013 | Patrick et al. |
| 2013/0096495 A1 | 4/2013 | Holmqvist et al. |
| 2013/0123719 A1 | 5/2013 | Mao et al. |

(56)                References Cited

U.S. PATENT DOCUMENTS

| | | |
|---|---|---|
| 2013/0158430 A1 | 6/2013 | Aceti et al. |
| 2013/0178826 A1 | 7/2013 | Li |
| 2013/0190683 A1* | 7/2013 | Hanson ............. A61M 5/14248 |
| | | 604/67 |
| 2013/0216989 A1 | 8/2013 | Cuthbert |
| 2013/0253430 A1 | 9/2013 | Kouyoumjian et al. |
| 2013/0302398 A1 | 11/2013 | Ambati et al. |
| 2013/0311917 A1 | 11/2013 | Bar-or et al. |
| 2013/0317384 A1 | 11/2013 | Le |
| 2013/0328572 A1 | 12/2013 | Wang et al. |
| 2013/0345633 A1 | 12/2013 | Chong |
| 2014/0039396 A1 | 2/2014 | Geipel et al. |
| 2014/0046288 A1 | 2/2014 | Geipel et al. |
| 2014/0073883 A1 | 3/2014 | Rao et al. |
| 2014/0088554 A1 | 3/2014 | Li et al. |
| 2014/0099614 A1 | 4/2014 | Hu et al. |
| 2014/0100241 A1 | 4/2014 | Slater et al. |
| 2014/0163521 A1 | 6/2014 | O'Conner |
| 2014/0200525 A1 | 7/2014 | DiPierro |
| 2014/0206327 A1 | 7/2014 | Ziemianska et al. |
| 2014/0207047 A1 | 7/2014 | DiPierro et al. |
| 2014/0228736 A1 | 8/2014 | Eppstein et al. |
| 2014/0237028 A1 | 8/2014 | Messenger et al. |
| 2014/0240124 A1 | 8/2014 | Bychkov |
| 2014/0266584 A1 | 9/2014 | Ingle et al. |
| 2014/0272844 A1 | 9/2014 | Hendriks et al. |
| 2014/0272845 A1 | 9/2014 | Hendriks et al. |
| 2014/0272846 A1 | 9/2014 | Richling |
| 2014/0275135 A1 | 9/2014 | Genov et al. |
| 2014/0275932 A1 | 9/2014 | Zadig |
| 2014/0276127 A1 | 9/2014 | Ferdosi et al. |
| 2014/0279740 A1 | 9/2014 | Wernevi et al. |
| 2014/0302121 A1 | 10/2014 | Bevier |
| 2014/0303574 A1 | 10/2014 | Knutson |
| 2014/0365408 A1 | 12/2014 | Snyder et al. |
| 2014/0378943 A1 | 12/2014 | Geipel |
| 2015/0057616 A1 | 2/2015 | Shergold et al. |
| 2015/0209783 A1 | 7/2015 | Ingber et al. |
| 2015/0273148 A1 | 10/2015 | Sexton et al. |
| 2015/0310760 A1 | 10/2015 | Knotts et al. |
| 2015/0322939 A1 | 11/2015 | Katase |
| 2015/0342900 A1 | 12/2015 | Putnins |
| 2016/0030412 A1 | 2/2016 | Azhir |
| 2016/0058939 A1 | 3/2016 | Brewer et al. |
| 2016/0220553 A1 | 8/2016 | Azhir |
| 2016/0220798 A1* | 8/2016 | Netzel ............... A61M 5/14248 |
| 2016/0227361 A1 | 8/2016 | Booth et al. |
| 2016/0228383 A1 | 8/2016 | Zhang et al. |
| 2016/0235732 A1 | 8/2016 | Quik et al. |
| 2016/0235916 A1 | 8/2016 | Edwards et al. |
| 2016/0263312 A1 | 9/2016 | Junod et al. |
| 2016/0310664 A1 | 10/2016 | McKenzie et al. |
| 2016/0317057 A1 | 11/2016 | Li et al. |
| 2016/0317738 A1 | 11/2016 | Cross et al. |
| 2016/0339174 A1 | 11/2016 | Shapley et al. |
| 2016/0346456 A1 | 12/2016 | Cefal et al. |
| 2016/0346462 A1 | 12/2016 | Adams et al. |
| 2017/0007550 A1 | 1/2017 | Enscore et al. |
| 2017/0079932 A1 | 3/2017 | Emgenbroich et al. |
| 2017/0100573 A1 | 4/2017 | DiPierro |
| 2017/0189348 A1 | 7/2017 | Lee et al. |
| 2017/0189534 A1 | 7/2017 | Lee et al. |
| 2017/0207825 A1 | 7/2017 | Belogolovy |
| 2017/0209429 A1 | 7/2017 | Stinchcomb et al. |
| 2017/0232192 A1 | 8/2017 | Sasaki |
| 2017/0249433 A1 | 8/2017 | Hagen et al. |
| 2017/0296107 A1 | 10/2017 | Reid et al. |
| 2017/0296317 A1* | 10/2017 | Gordon ................. A61M 5/445 |
| 2017/0351840 A1 | 12/2017 | Goguen |
| 2018/0014783 A1 | 1/2018 | Shi et al. |
| 2018/0028069 A1 | 2/2018 | Shi et al. |
| 2018/0028070 A1 | 2/2018 | Shi |
| 2018/0028071 A1 | 2/2018 | Shi |
| 2018/0028072 A1 | 2/2018 | Shi |
| 2018/0110768 A1 | 4/2018 | Quik et al. |
| 2018/0110975 A1 | 4/2018 | Ivanoff et al. |
| 2018/0165566 A1 | 6/2018 | Rogers et al. |
| 2018/0168504 A1 | 6/2018 | Ding et al. |
| 2018/0197637 A1 | 7/2018 | Chowdhury |
| 2018/0374381 A1 | 12/2018 | Darmour et al. |
| 2019/0000828 A1 | 1/2019 | Azhir |
| 2019/0009019 A1 | 1/2019 | Shor et al. |
| 2019/0054078 A1 | 2/2019 | Azhir et al. |
| 2019/0054235 A1 | 2/2019 | DiPierro et al. |
| 2019/0231707 A1 | 8/2019 | Stiles et al. |
| 2019/0374482 A1 | 12/2019 | Schaller et al. |
| 2020/0030590 A1 | 1/2020 | Buchman et al. |
| 2020/0368175 A1 | 11/2020 | Arora et al. |
| 2021/0169822 A1 | 6/2021 | Zumbrunn et al. |
| 2022/0001158 A1 | 1/2022 | Ruane et al. |
| 2022/0280763 A1 | 9/2022 | Johnston et al. |
| 2023/0277767 A1 | 9/2023 | DiPierro et al. |

FOREIGN PATENT DOCUMENTS

| | | |
|---|---|---|
| CA | 2142871 A1 | 3/1994 |
| CN | 1704056 A | 12/2005 |
| DE | 19958554 A1 | 1/2001 |
| DE | 10105759 C1 | 10/2001 |
| DE | 10103158 A1 | 8/2002 |
| EP | 311313 A2 | 4/1989 |
| EP | 0314528 B1 | 12/1992 |
| EP | 0354554 B1 | 1/1994 |
| EP | 0726005 A1 | 8/1996 |
| EP | 857725 A1 | 8/1998 |
| EP | 870768 A1 | 10/1998 |
| EP | 955301 A2 | 11/1999 |
| EP | 0612525 B1 | 9/2001 |
| EP | 1815784 A1 | 8/2007 |
| EP | 1977746 B1 | 7/2014 |
| EP | 1662989 B1 | 9/2014 |
| EP | 3016586 A2 | 5/2016 |
| GB | 1528391 A | 10/1978 |
| GB | 2030862 A | 4/1980 |
| GB | 2142822 A | 1/1985 |
| GB | 2230439 A | 10/1990 |
| JP | 02202813 A | 8/1990 |
| JP | H09504974 A | 5/1997 |
| JP | 09512006 A | 12/1997 |
| JP | 2000515394 A | 11/2000 |
| JP | 2001505491 A | 4/2001 |
| JP | 2002092180 A | 3/2002 |
| JP | 2003506477 A | 2/2003 |
| JP | 2005521526 A | 7/2005 |
| JP | 2005525147 A | 8/2005 |
| JP | 2007509661 A | 4/2007 |
| JP | 2008523918 A | 7/2008 |
| JP | 2009544338 A | 12/2009 |
| JP | 2010/507457 | 3/2010 |
| JP | 2010518914 A | 6/2010 |
| JP | 2010279808 A | 12/2010 |
| JP | 2011036491 A | 2/2011 |
| JP | 2013524951 A | 6/2013 |
| JP | 2015070868 A | 4/2015 |
| JP | 2016202904 A | 12/2016 |
| KR | 20180011653 A | 2/2018 |
| WO | WO86/07269 A1 | 12/1986 |
| WO | WO88/003803 A1 | 6/1988 |
| WO | WO91/14441 A1 | 10/1991 |
| WO | WO92/021339 A1 | 12/1992 |
| WO | WO94/008992 A1 | 4/1994 |
| WO | WO94/010987 A1 | 5/1994 |
| WO | WO95/06497 A1 | 3/1995 |
| WO | WO96/015123 A1 | 5/1996 |
| WO | WO96/040682 A1 | 12/1996 |
| WO | WO97/011072 A1 | 3/1997 |
| WO | WO97/011073 A1 | 3/1997 |
| WO | WO97/11741 A1 | 4/1997 |
| WO | WO97/18782 A1 | 5/1997 |
| WO | WO97/019059 A1 | 5/1997 |
| WO | WO97/028801 A1 | 8/1997 |
| WO | WO97/034605 A1 | 9/1997 |
| WO | WO97/042941 A2 | 11/1997 |
| WO | WO97/046554 A1 | 12/1997 |

(56) References Cited

FOREIGN PATENT DOCUMENTS

| | | |
|---|---|---|
| WO | WO98/042713 A1 | 10/1998 |
| WO | WO98/46093 A1 | 10/1998 |
| WO | WO98/054152 A1 | 12/1998 |
| WO | WO98/054181 A1 | 12/1998 |
| WO | WO98/054182 A1 | 12/1998 |
| WO | WO98/054189 A1 | 12/1998 |
| WO | WO98/55107 A1 | 12/1998 |
| WO | WO99/002517 A1 | 1/1999 |
| WO | WO99/003859 A1 | 1/1999 |
| WO | WO99/021834 A1 | 5/1999 |
| WO | WO99/024422 A1 | 5/1999 |
| WO | WO99/066916 A1 | 12/1999 |
| WO | WO00/010997 A1 | 3/2000 |
| WO | WO00/032600 A1 | 6/2000 |
| WO | WO00/034279 A1 | 6/2000 |
| WO | WO00/034284 A1 | 6/2000 |
| WO | WO00/035279 A1 | 6/2000 |
| WO | WO00/035456 A1 | 6/2000 |
| WO | WO00/044755 A1 | 8/2000 |
| WO | WO00/064885 A1 | 11/2000 |
| WO | WO00/066596 A1 | 11/2000 |
| WO | WO00/74763 A2 | 12/2000 |
| WO | WO00/74933 A1 | 12/2000 |
| WO | WO01/005459 A1 | 1/2001 |
| WO | WO01/037814 A1 | 5/2001 |
| WO | WO02/076211 A1 | 10/2002 |
| WO | WO03/022349 A2 | 3/2003 |
| WO | WO03/026655 A1 | 4/2003 |
| WO | WO03/055486 A1 | 7/2003 |
| WO | WO03/061656 A1 | 7/2003 |
| WO | WO03/070191 A1 | 8/2003 |
| WO | WO03/097146 A1 | 11/2003 |
| WO | WO2004/024124 A1 | 3/2004 |
| WO | WO2004/073429 A1 | 9/2004 |
| WO | WO2005/023227 A2 | 3/2005 |
| WO | WO2005/079161 A2 | 9/2005 |
| WO | WVO2006/069097 A2 | 6/2006 |
| WO | WO2007/013975 A2 | 2/2007 |
| WO | WO2007/041544 A1 | 4/2007 |
| WO | WO2007/104574 A2 | 9/2007 |
| WO | WO2007/104575 A2 | 9/2007 |
| WO | WO2007/133141 A1 | 11/2007 |
| WO | WO2008/024408 A2 | 2/2008 |
| WO | WO2008/054788 A2 | 5/2008 |
| WO | WO2008/069921 A2 | 6/2008 |
| WO | WO2008/069970 A2 | 6/2008 |
| WO | WO2008/069972 A2 | 6/2008 |
| WO | WO2008/122049 A2 | 10/2008 |
| WO | WO2008/135283 A1 | 11/2008 |
| WO | WO2009/136304 A2 | 11/2009 |
| WO | WO2011/088072 A2 | 7/2011 |
| WO | WO2012/012846 A1 | 2/2012 |
| WO | WO2012/101060 A1 | 8/2012 |
| WO | WO2013/093666 A1 | 6/2013 |
| WO | WO2013/168068 A1 | 11/2013 |
| WO | WO2014/001877 A1 | 1/2014 |
| WO | WO2014/043502 A1 | 3/2014 |
| WO | WO-2015094945 A1 * | 6/2015 ............ A61M 39/02 |
| WO | WO2016/081616 A2 | 5/2016 |
| WO | WO2016/132368 A1 | 8/2016 |
| WO | WO2016/161416 A1 | 10/2016 |
| WO | WO-2016181384 A2 * | 11/2016 .......... A61M 5/1407 |
| WO | WO2017/053938 A1 | 3/2017 |
| WO | WO2017/125455 A1 | 7/2017 |
| WO | WO2018/026759 A1 | 2/2018 |
| WO | WO2018/129363 A1 | 7/2018 |
| WO | WO2018/133786 A1 | 7/2018 |
| WO | WO2019/090125 A2 | 5/2019 |

OTHER PUBLICATIONS

Ahlskog et al.; Frequency of levodopa-related dyskinesias and motor fluctuations as estimated from the cumulative literature; Movement Disorders; 16(3); pp. 448-458, May 1, 2001.

Angulo et al.; Oral nicotine in treatment of primary sclerosing cholangitis: a pilot study; Digestive diseases and sciences; 44(3); pp. 602-607; Mar. 1, 1999.

Azhir, Arasteh; U.S. Appl. No. 62/320,871 entitled "Compositions and methods for treatment related to fall and fall frequency in neurodegenerative diseases", filed Apr. 11, 2016.

Baldessarini et al.; Preclinical studies of the pharmacology of aporphines; In: Gessa GL, Corsini GU, eds.; Apomorphine and other dopaminomi-'metics vol. 1, Basic pharmacology; New York: Raven Press; pp. 219-228; (the year of publication is sufficiently earlier than the effective U.S. filing date and any foreign priority date so that the particular month of publication is not in issue) 1981.

Balfour et al.; Pharmacology of nicotine and its therapeutic use in smoking cessation and neurodegenerative disorders; Pharmacology and Therapeutics; 72(1); pp. 51-81; Jan. 1, 1996.

Benowitz et al.; Sources of variability in nicotine and cotinine levels with use of nicotine nasal spray, transdermal nicotine, and cigarette smoking; British Journal of Clinical Pharmacology; 43(3); pp. 259-267; Mar. 1, 1997.

Benowitz et al.; Stable isotope studies of nicotine kinetics and bioavailability; Clin Pharm and Ther; 49(3); pp. 270-277; Mar. 1991.

Bordia et al.; Continuous and intermittent nicotine treatment reduces L-3 4-dihydroxyphenylalanine (L-DOPA)-induced dyskinesias in rat model of Parkinson's diseases; Journal of Pharmacology ans Experimental Therapeutics; 327(1); pp. 239-247; Oct. 1, 2008.

Bordia et al.; Partial recovery of striatal nicotinic receptors in I-methyl-4-phenyl-1,2,3,6-tetrahydropyridine (MPTP)-lesioned monkeys with chronic oral nicotinic; The Journal of Pharmacology and Experimental Therapeutics; 319(1); pp. 285-292; Oct. 1, 2006.

Bove et al.; Toxin-induced models of Parkinson's disease; NeuroRx; 2(3); pp. 484-494; Jul. 31, 2005.

Bricker et al.; Randomized controlled pilot trial of a smartphone app for smoking cessation using acceptance and commitment therapy; Drug and Alcohol Dependence; 143; pp. 87-94; Oct. 1, 2014 (Author Manuscript).

Brotchie et al.; Levodopa-induced dyskinesia in Parkinson's disease; Journal of Neural Transmission; 112(3); pp. 359-391; Mar. 1, 2005.

Bruguermolle; Chronopharmacokinetics; Clin Pharmacokinet; 35(2); pp. 83-94; Aug. 1998.

Calabresi et al.; Levodopa-induced dyskinesias inpatients with parkinson's disease: filling the bench-to-bedside gap; The Lancet Neurology; 9(11); pp. 1106-1117; Nov. 1, 2010.

Carta et al.; Role of striatal L-DOPA in the production of dyskinesia in 6-hydroxydopamine lesioned rats; Journal of Neurochemistry; 96(6); pp. 1718-1727; Mar. 2006.

Chen et al.; Enhanced striatal opioid receptor-mediated G-protein activation in L-DOPA-treated dyskinetic monkeys; Neuroscience; 132(2); pp. 409-420; Dec. 31, 2005.

Damaj et al.; Antinociceptive responses to nicotinic acetylcholine receptor ligands after systemic and intrathecal administration in mice; Journal of Pharmacology and Experimental Therapeutics; 284(3); pp. 1058-1065; Mar. 1, 1998.

Davie; A review of Parkinson's disease. British Medical Bulletin 2008 86(1): 109-127; Apr. 8, 2008.

De La Fuente et al.; The placebo effect in Parkinson's disease; Trends in Neuroscience; 25(6); pp. 302-306; Jun. 1, 2002.

Di Monte et al.; Relationship among nigrostriatal denervation, parkinsonism, and dyskinesias in the MPTP primate model; Movement Disorders; 15(3); pp. 459-466; May 1, 2000.

Dockser-Marcus, A.; New research shows drugs work best at certain times; The Wall Street Journal; 6 pgs.; May 27, 2003; (http://www.wsj.com/articles/SB105397312486508700).

Domino et al.; Nicotine alone and in combination with L-DOPA methyl ester or the D(2) agonist N-0923 in MPTP-induced chronic hemiparkinsonian monkeys; Exp Neurol; 158(2); pp. 414-421; Aug. 1999.

Dutil; Benzoyl Peroxide: Enhancing antibiotic efficacy in acne management; Skin Therapy Letter; 15(1); pp. 5-7; Nov./Dec. 2010.

Ebersbach et al.; Worsening of motor performance in patients with Parkinson's disease following transdermal nicotine administration; Movement Disorders; 14(6); pp. 1011-1013; Nov. 1, 1999.

(56)                References Cited

OTHER PUBLICATIONS

Ethicon Endo-Surgery, Inc.; Sedasys® Computer-assisted personalized sedation system essential product information; retrieved May 12, 2015 from the internet (http://www.sedasys.com/explore-the-system/essential-product-information); 2 pgs.

Fagerstrom et al.; Nicotine may relieve symptoms of Parkinson's disease; Psychopharmacology; 116(1); pp. 117-119; Sep. 16, 1994.

Food and Drug Administration; Guidance for Industry—Dissolution Testing of Immediate Release Solid Oral Dosage Forms; 17 pages; retrieved from the internet (https://www.fda.gov/downloads/drugs/guidances/ucm070237.pdf); Aug. 1997.

Gatto et al.; TC-1734: An orally active neuronal nicotinic acetylcholine receptor modulator with antidepressant, neuroprotective and long-lasting cognitive effects; CNS Drug Reviews; 10(2); pp. 147-166; Jun. 1, 2004.

Gennaro (Editor); Remington: The Science and Practice of Pharmacy; 19th Ed.; Mack Publishing Co.; Easton, PA; p. 1582-1584; Jun. 1995.

Giannos; Chapter 20: Pulsatile fSmartf Drug Delivery, in Skin Delivery Systems: Transdermals, Dermatologicals, and Cosmetic Actives; (ed.) Wille, Jr; Blackwell Pub.; Oxford, UK; pp. 327-357; Jun. 2006.

Gora; Nicotine transdermal systems; The Annals of Pharmacotherapy; 27(6); pp. 742-750; Jun. 1993.

Gotti et al.; Brain nicotinic acetylcholine receptors: native subtypes and their relevance; Treands in Pharmacological Sciences; 27(9); pp. 482-491; Sep. 30, 2006.

Green et al.; An oral formulation of nicotine for release and absorption in the colon: its development and pharmacokinetics. British Journal of Clinical Pharmacology; 48(4); pp. 485-493; Oct. 1999.

Gries et al.; Importance of Chronopharmacokinetics in Design and Evaluation of Transdermal Drug Delivery Systems; J Pharmacol Exp Ther; 285(2); pp. 457-463; May 1998.

Guy; Current status and future prospects of transdermal drug delivery; Pharm Res; 13(12); pp. 1765-1769; Dec. 1996.

Halberg et al.; Chronomics: circadian and circaseptan timing of radiotherapy, drugs, calories, perhaps nutriceuticals and beyond; Journal of Experimental Therapeutics and Oncology; 3(5); pp. 223-260; Sep. 2003.

He et al.; Autoradiographic analysis of dopamine receptor-stimulated [35S]GTPtS binding in rat striatum; Brain Research; 885(1); pp. 133-136; Dec. 1, 2000.

He et al; Autoradiographic analysis of N-methyl-D-aspartate receptor binding in monkey brain: Effects of I-methyl-4-phenyl-I,2,3,6-tetrahydropyridine andlevodopa treatment; Neuroscience; 99(4); pp. 697-704; Aug. 23, 2000.

Heffner et al.; Feature-level analysis of a novel smartphone applicationn for smoking cessation; Am. J. Drug Alcohol Abuse; 41(1); pp. 68-73; Jan. 2015 (Author Manuscript).

Hrushesky; Temporally optimizable delivery systems: sine qua non for the next therapeutic revolution; J Cont Rel; 19(1-3); pp. 363-368; Mar. 1992.

Hsu et al.; Effect of the D3 dopamine receptor partial agonist BP897 [N-[4-(4-(2-methoxyphenyl)piperazinyl)butyl]-2-napthamide] on L-3,4-dihydroxyphenylalanine-induced dyskinesias and parkinsonism in squirrel monkeys; The Journal of Pharmacology and Experimental Therapeutics. 311(2); pp. 770-777; Nov. 1, 2004.

Huang et al.; Inhibitory effects of curcumin on in vitro lipoxygenase and cyclooxygenase activities in mouse epidermis; Cancer Res; 51(3); pp. 813-819; Feb. 1991.

Hukkanen et al.; Metabolism and disposition kinetics of nicotine; Pharmacological Reviews; 57(1); pp. 79-115; Mar. 1, 2005.

Hurley; Growing list of positive effects of nicotine seen in neurodegenerative disorders; Neurology Today; 12(2); pp. 37-38; Jan. 19, 2012.

Ingram et al.; Preliminary observations of oral nicotine therapy for inflammatory bowel disease: an open-label phase I-II study of tolerance; Inflamm Bowel Diseases; 11(12); pp. 1092-1096; Dec. 1, 2005.

Janson et al.; Chronic nicotine treatment counteracts dopamine D2 receptor upregulation induced by a partial meso-diencephalic hemitransection in the rat; Brain Res.; 655(1-2); pp. 25-32; Aug. 29, 1994.

Jarvik et al.; Inhibition of cigarette smoking by orally administered nicotine; Clinical Pharmacology and Therapeutics; 11(4); pp. 574-576; Jul. 1, 1970.

Jeyarasasingam et al.; Nitric oxide is involved in acetylcholinesterase inhibitor-induced myopathy in rats; The Journal of Pharmacology and Experimental Therapeutics; 295(1); pp. 314-320; Oct. 1, 2000.

Jeyarasasingam et al.; Stimulation of non-o7 nicotinic receptors partially protects dopaminergic neurons from I-methyl-4-phenylpyridinium-induced toxicity in culture; Neuroscience; 109(2); pp. 275-285; Jan. 28, 2002.

Jeyarasasingam et al.; Tacrine, a reversible acetylcholinesterase inhibitor, induces myopathy; Neuroreport; 11(6); pp. 1173-1176; Apr. 27, 2000.

Kalish et al.; Prevention of contact hypersensitivity to topically applied drugs by ethacrynic acid: potential application to transdermal drug delivery; J. Controll Rel; 48(1); pp. 79-87; Sep. 1997.

Kalish et al.; Sensitization of mice to topically applied drugs: albuterol, chlorpheniramine, clonidine and nadolol; Contact Dermatitis; 35(2); pp. 76-82; Aug. 1996.

Kelton et al.; The effects of nicotine on Parkinson's disease; Brain Cognition; 43(1-3); pp. 274-282; Jun. 2000.

Kennelly; Microcontrollers drive home drug delivery; 3 pgs; posted Jul. 2014; (retrieved Jul. 26, 2016 from the internet: http://electronicsmaker.com/microcontrollers-drive-home-drug-delivery-2.

Kiwi Drug; Buy nicorette microtabs; 3 pages; retrieved from the internet (www.kiwidrug.com/search/nicorette_microtabs); on Jul. 26, 2018.

Kotwal; Enhancement of intophoretic transport of diphenhydramine hydrochloride thermosensitive gel by optimization of pH, polymer concentration, electrode design, and pulse rate; AAPS PharmSciTech; 8(4); pp. 320-325; Oct. 2007.

Kulak et al.; 5-Iodo-A-85380 binds to oconotoxin Mil-sensitive nicotinic acetylcholine receptors (nAChRs) as well as o4j32 subtypes; Journal of Neurochemistry; 81(2); pp. 403-406; Apr. 1, 2002.

Kulak et al.; Declines in different pi nicotinic receptor populations in monkey striatum after nigrostriatal damage; The Journal of Pharmacology and Experimental Therapeutics; 303(2); pp. 633-639; Nov. 1, 2002.

Kulak et al.; Loss of nicotinic receptors in monkey striatum after I-methyl-4-phenyl-1,2,3,6-tetrahydropyridine treatment is due to a decline in oconotoxin Mil sites; Molecular Pharmacology; 61(1); pp. 230-238; Jan. 1, 2002.

Kumar et al.; Levodopa-dyskinesia incidence by age of Parkinson's disease onset; Movement disorders; 20(3); pp. 342-344; Mar. 2005.

Kydonieus et al. (Editors); Biochemical Modulation of Skin Reactions; CRC Press; Boca Ratan, FL; pp. 9-10; Dec. 1999.

Labrecque, G. et al.; Chronopharmacokinetics; Pharmaceutical News; 4(2); pp. 17-21; (year of pub. sufficiently earlier than effective US filing date and any foreign priority date) 1997.

Lai et al.; Long-term nicotine treatment decreases striatal a6 nicotinic acetylcholine receptor sites and function in mice; Molecular Pharmacology; 67(5); pp. 1639-1647; May 1, 2005.

Lai et al.; Selective recovery of striatal 1251-a-conotoxinMII nicotinic receptors after nigrostriatal damage in monkeys; Neuroscience; 127(2); pp. 399-408; Dec. 31, 2004.

Lamberg; Chronotherapeutics: Implications for drug therapy; American Pharmacy; NS31(11); pp. 20-23; Nov. 1991.

Langston et al.; Investigating levodopa-induced dyskinesias in the parkinsonian primate; Annals of Neurology; 47(4 Suppl 1); pp. S79-S88; Apr. 2000.

Laser et al.; A review of micropumps; J. of Micromech. And Microeng.; 14; pp. R35-R64; Apr. 2004.

Lee et al.; A comprehensive review of opioid-induced hyperalgesia; Pain Physician; 14; pp. 145-161; Mar. 2011.

Lemay et al.; Lack of efficacy of a nicotine transdermal treatment on motor and cognitive deficits in Parkinson's disease; Prog Neuropsychopharmacol Biol Psychiatry; 28(1); pp. 31-39; Jan. 2004.

(56)                References Cited

OTHER PUBLICATIONS

Lemmer; Clinical Chronopharmacology: The Importance of Time in Drug Treatment, in Ciba Foundation Symposium 183—Circadian Clocks and their Adjustment (eds. Chadwick and Ackrill); John Wiley & Sons, Inc.; pp. 235-253; Apr. 1995.
Lemmer; Implications of chronopharmacokinetics for drug delivery: antiasthmatics, H2-blockers and cardiovascular active drugs; Adv Drug Del Rev, 6(1); pp. 83-100; Jan./Feb. 1991.
Lemmer; The clinical relevance of chronopharmacology in therapeutics; Pharmacological Research; 33(2); pp. 107-115; Feb. 1996.
LeWitt et al.; New developments in levodopa therapy; Neurology; 62(No. 1, Suppl. 1); pp. S9-S16; Jan. 2004.
Lieber Man; Compressed tablets by direct compression; Pharmaceutical Dosage forms; vol. 1, 2nd ed.; Marcel Dekker Inc.; pp. 195-246; (the year of publication is sufficiently earlier than the effective U.S. filing date and any foreign priority date so that the particular month of publication is not in issue) 1989.
Lieberman; Compression-coated and layer tablets; Pharmaceutical Dosage forms; vol. 1, 2nd ed.; Marcel Dekker Inc.; pp. 266-271; (the year of publication is sufficiently earlier than the effective U.S. filing date and any foreign priority date so that the particular month of publication is not in issue) 1989.
Lundblad et al.; Cellular and behavioural effects of the adenosine A2a receptor antagonist KW-6002 in a rat model of I-DOPA-induces Dyskinesia; Journal of Neurochemistry; 84(6); pp. 1398-1410; Mar. 2003.
Madandla et al,; Voluntary running provides neuroprotection in rats after 6-hydroxydopamine injection into the medial forebrain bundle; Metabolic Brain Disease; 19(1-2); pp. 43-50; Jun. 2004.
Maillefer et al.; A high-performance silicon micropump for an implantable drug delivery system; 12th IEEE Int'l Conf. on Micro Electro Mechanical Systems; MEMS '99; Orlando, FL; pp. 541-546; Jan. 1999.
Matta et al.; Guidelines on nicotine dose selection for in vivo research; Psychopharmacology (Berl.); 190(3); pp. 269-319; Feb. 1, 2007.
Mccallum et al,; Decrease in alpha3/alpha6 nicotinic receptors in monkey brain after nigrostriatal damage; Molecular Pharmacology; 68(3); pp. 737-746; Sep. 2005.
Mccallum et al.; Compensation in pre-synaptic dopaminergic function following nigrostriatal damage in primates; Journal of Neurochemistry; 96(4); pp. 960-972; Feb. 1, 2006.
Mccallum et al.; Differential regulation of mesolimbic alpha 3/alpha 6 beta 2 and aplha 4 beta 2 nicotinic acetylcholine receptor sites and function after long-term oral nicotine to monkeys; The Journal of Pharmacology and Experimental Therapeutics; 318(1); pp. 381-388; Jul. 2006.
Mccallum et al.; Increases in aplha 4 but not aplha3/alpha6 nicotinic receptor sites and function in the primate striatum following chronic oral nicotine treatment; Journal of Neurochemistry; 96(4); pp. 1028-1041; Feb. 2006.
McNeil Sweden AB. Package Leaflet: Information for the user. Nicorette Microtab Lemon 2mg sublingual tablets. (This leaflet was last approved in Apr. 16, 2008). retrived from ( www.lakemedelsverket. se/SPC_PIL/Pdf/enhumpil/Nicorette%20Microtab%20Lemon% 202mg%20sublingual%20tablet%20ENG.pdf.) Accessed Aug. 19, 2010.
Medtronic; MiniMed Paradigm® Veo(TM) System (product info.); retrieved May 12, 2015from the internet: (http://www.medtronic. co.uk/your-health/diabetes/device/insulin-pumps/paradigm-veo-pump/ ); 3 pgs.
Meissner et al.; Priorities in parkinson's disease research; Nature reviews Drug Discovery: 10(5); pp. 377-393; May 1, 2011.
Menzaghi et al.; Interactions between a novel cholinergic ion channel against, SIB-1765F anf L-DOPA in the reserpine model of parkinson's disease in rats; Journal of Pharmacology and Experimental Therapeutics; 280(1); pp. 393-401; Jan. 1, 1997.
Merck manual of therapy and diagnosis; 17th edition. Merck Research Laboratories; pp. 1466-1471; (the year of publication is sufficiently earlier than the effective U.S. filing date and any foreign priority date so that the particular month of publication is not in issue) 1999.
Meredith et al.; Behavioral models of Parkinson's disease in rodents: a new look at an old problem; Movement Disorders; 21(10); pp. 1595-1606; Oct. 1, 2006.
Meshul et al.; Nicotine Affects Striatal Glutamatergic Function in 6-OHDA Lesioned Rats; Advanced in behavioural Biology. Basal Ganglia VI.; Springer, Boston, MA.; vol. 54; pp. 589-598; the year of publication is sufficiently earlier than the effective U.S. filing date and any foreign priority date so that the particular month of publication is not in issue) 2002.
Meshul et al.; Nicotine alters striatal glutamate function and decreases the apomorphine-induced contralateral rotations in 6-OHDA-lesioned rats; Experimental Neurology; 175(1); pp. 257-274; May 31, 2002.
Molander et al.; Reduction of tobacco withdrawal symptoms with a sublingual nicotine tablet: A placebo controlled study; Nictonie & Tob. Res.; 2(2); pp. 187-191; May 2000.
Murphy et al.; Transdermal drug delivery systems and skin sensitivity reactions. Incidence and management; Am. J. Clin Dermatol.; 1(6); pp. 361-368; Nov./Dec. 2000.
Mutalik et al.; Glibenclamide transdermal patches: physicochemical, pharmacodynamic, and pharmacokinetic evaluation; J Pharm Sci; 93(6); pp. 1577-1594; Jun. 2004.
Mutalik et al.; Glipizide matrix transdermal systems for diabetes mellitus: preparation, in vitro and preclinical studies; Life Sci; 79(16; pp. 1568-1567; Sep. 2006.
Nakadate et al.; Effects of chalcone derivatives on lipoxygenase and cyclooxygenase activities of mouse epidermis; Prostaglandins; 30(3); pp. 357-368; Sep. 1985.
National Institute of Neurological Disorders and Stroke. Parkinson's Disease: Hope Through Research. 54 pages; Retrieved from the internet (https://catalog.ninds.nih.gov/pubstatic//15-139/15-139. pdf) on Jan. 15, 2018.
Newhouse et al.; Nicotine treatment of mild cognitive impairment: a 6-month double-blind pilot clinical trial; Neurology; 78(2); pp. 91-101; Jan. 10, 2012.
Newmark; Plant phenolics as potential cancer prevention agents; Chapter 3 in Dietary Phytochemicals in Cancer Prevention; Chap. 3; Adv. Exp. Med. Biol. 401; pp. 25-34; © 1996.
Ohdo; Changes in toxicity and effectiveness with timing of drug administration: implications for drug safety; Drug Safety; 26(14); pp. 999-1010; Dec. 2003.
Olanow; The scientific basis for the current treatment of Parkinson's disease; Annu. Rev. Med .; 55; pp. 41-60; Feb. 18, 2004.
Olsson et al.; A valve-less planar pump in silicon; IEEE; The 8th International Conference on Solid-State Sensors and Actuators; vol. 2; pp. 291-294, Jun. 1995.
Olsson et al.; An improved valve-less pump fabricated using deep reactive ion etching; Proc. Of the IEEE, 9th Int'l Workshop on MEMS; San Diego, CA; pp. 479-484; Feb. 11-15, 1996.
O'Neill et al.; The role of neuronal nicotinic acetylcholine receptors in acute and chronic neurodegeneration; Current Drug Targets—CNS and Neurological Disorders; 1(4); pp. 399-412; Aug. 1, 2002.
Parkinson Study Group; Levodopa and the progression of Parkinson's disease; N Engl J Med.; 351; pp. 2498-2508; Dec. 9, 2004.
Petzinger et al.; Reliability and validity of a new global dyskinesia rating scale in the MPTP-lesioned non-human primate; Movement Disorders; 16(2); pp. 202-207; Mar. 1, 2001.
Priano et al.; Nocturnal anomalous movement reduction and sleep microstructure analysis in parkinsonian patients during 1-night transdermal apomorphine treatment; Neurol Sci.; 24(3); pp. 207-208; Oct. 2003.
Prosise et al.; Effect of abstinence from smoking on sleep and daytime sleepiness; Chest; 105(4); pp. 1136-1141; Apr. 1994.
Quik et al.; Chronic oral nicotine normalizes dopaminergic function and synaptic plasticity in I-methyl-4-phenyl-I,2,3,6-tetrahydropyridine-lesioned primates; The Journal of Neuroscience; 26(17); pp. 4681-4689; Apr. 26, 2006.
Quik et al.; Chronic oral nicotine treatment protects against striatal degeneration in MPTP-treated primates; Journal of Neurochemistry; 98(6); pp. 1866-1875; Sep. 1, 2006.

(56) References Cited

OTHER PUBLICATIONS

Quik et al.; Differential alterations in nicotinic receptor a6 and /33 subunit messenger RNAs in monkey substantia nigra after nigrostriatal degeneration; Neuroscience; 100(1); pp. 63-72; Sep. 7, 2000.

Quik et al.; Differential declines in striatal nicotinic receptor subtype function after nigrostriatal damage in mice; Molecular Pharmacology; 63(5); pp. 1169-1179; May 1, 2003.

Quik et al.; Differential nicotinic receptor expression in monkey basal ganglia: Effects of nigrostriatal damage; Neuroscience; 112(3); pp. 619-630; Jul. 5, 2002.

Quik et al.; Expression of D3 receptor messenger RNA and binding sites in monkey striatum and substantia nigra after nigrostriatal degeneration: Effect of levodopa treatment.;Neuroscience; 98(2); pp. 263-273; Jun. 30, 2000.

Quik et al.; Increases in striatal preproenkephalin gene expression are associated with nigrostriatal damage but not L-DOPA-induced dyskinesias in the squirrel monkey; Neuroscience; 113(1); pp. 213-220; Aug. 2, 2002.

Quik et al.; L-DOPA treatment modulates nicotinic receptors in monkey striatum; Mol Pharmacol; 64(3); pp. 619-628; Sep. 2003.

Quik et al.; Localization of nicotinic receptor subunit mRNAs in monkey brain by in situ hybridization; The Journal of Comparative Neurology; 425(1); pp. 58-69; Sep. 11, 2000.

Quik et al.; Loss of a-conotoxinMII- and A85380-sensitive nicotinic receptors in Parkinson's disease striatum; Journal of Neurochemistry; 88(3); pp. 668-679; Feb. 1, 2004.

Quik et al.; Nicotine administration reduces striatal MPP+ levels in mice; Brain Research; 917(2); pp. 219-224; Nov. 2, 2001.

Quik et al.; Nicotine and nicotinic receptors; relevance to Parkinson's disease; Neurotoxicology; 23(4-5); pp. 581-594; Oct. 2002.

Quik et al.; Nicotine and Parkinson's disease: implications for therapy; Movement Disorders; 23(12); pp. 1641-1652; (Author Manuscript); Sep. 1, 2008.

Quik et al.; Nicotine as a potential neuroprotective agent for Parkinson's disease; Movement disorders; 27(8); pp. 947-957; Jul. 1, 2012.

Quik et al.; Nicotine neuroprotection against nigrostriatal damage: importance of the animal model; Trends in Pharmacological sciences; 28(5); pp. 229-235; May 31, 2007.

Quik et al.; Nicotine reduces levodopa-induced dyskinesias in lesioned monkeys; Annals of neurology; 62(6); pp. 588-596; (Author Manuscript); Dec. 1, 2007.

Quik et al.; Nicotinic receptors and Parkinson's disease; European Journal of Pharmacology; 393(1); pp. 223-230; Mar. 30, 2000.

Quik et al.; Striatal a6 nicotinic acetylcholine receptors: Potential targets for Parkinson's disease therapy; The Journal of Pharmacology and Experimental Therapeutics; 316(2); pp. 481-489; Feb. 1, 2006.

Quik et al.; Subunit composition of nicotinic receptors in monkey striatum: Effect of treatments with I-methyl-4-phenyl-I,2,3,6-tetrahydropyridine or L-DOPA; Molecular Pharmacology; 67(1); pp. 32-41; Jan. 2005.

Quik et al.; Vulnerability of 125I-a-conotoxin Mil binding sites to nigrostriatal damage in monkey; The Journal of Neuroscience; 21(15); pp. 5494-5500; Aug. 1, 2001.

Quik; Smoking, nicotine and Parkinson's disease; Trends in Neurosciences; 27 (9); pp. 561-568; Sep. 2004.

Redfern et al.; Circadian rhythms, jet lag, and chronobiotics: An overview; Chronobiology International; 11(4); pp. 253-265; Aug. 1994.

Reinberg; Concepts of Circadian Chronopharmacology; Annals of the New York Academy of Sciences; 618 (Temporal Control of Drug Delivery); pp. 102-115; Feb. 1991.

Rueter et al.; ABT-089: Pharmacological properties of a neuronal nicotinic acetylcholine receptor agonist for the potential treatment of cognitive disorders; CNS Drug Reviews; 10(2); pp. 167-182; Jun. 1, 2004.

Samii et al.; Parkinson's disease; The Lancet; 363(9423); pp. 1783-1793; May 29, 2004.

Savitt et al.; Diagnosis and treatment of Parkinson disease: molecules to medicine; The Journal of Clinical Investigation; 116(7); pp. 1744-1754; Jul. 3, 2006.

Schapira; Disease modification in Parkinson's disease; The Lancet Neurology; 3(6); pp. 362-368; Jun. 30, 2004.

Schneider et al.; Effects of SIB-1508Y, a novel neuronal nictonic acetylcholine receptor agonist, on motor behavior in parkinsonian monkeys; Movement Disorders; 13(4); pp. 637-642; Jul. 1, 1998.

Schneider et al.; Effects of the nicotinic acetylcholine receptor agonist SIB-1508Y on object retrieval performance in MPTP-treated monkeys: Comparison with levodopa treatment; Annals of Neurology; 43(3); pp. 311-317; Mar. 1, 1998.

Schober et al.; Classic toxin-induced animal models of Parkinson's disease: 6-OHDA and MPTP; Cell and Tissue Research; 318(1); pp. 215-224; Oct. 1, 2004.

Shin et al.; Enhanced bioavailability of triprolidine from the transdermal TPX matrix system in rabbits; Int. J. Pharm.; 234(1-2); pp. 67-73; Mar. 2002.

Silver et al.; Transdermal nicotine and haloperidol in Tourette's disorder: a double-blind placebo-controlled study; Journal of Clinical Psychiatry; 62(9); pp. 707-714; Sep. 1, 2001.

Singer et al.; Nightmares in patients with Alzheimer's disease caused by donepezil: Therapeutic effect depends on the time of intake; Nervenarzt; 76(9); pp. 1127-1129; Sep. 2005 (Article in German w/ Eng. Summary).

Star Micronics Co., LTD; Prototype Diaphragm Micro Pump SDMP305 (specifications); retrieved May 12, 2015 from the internet archive as of Jul. 2006 (http://www.star-m.jp/eng/products/develop/de07.htm); 3 pgs.

Stocchi et al.; Motor fluctuations in levodopa treatment: clinical pharmacology; European Neurology; 36(Suppl 1); pp. 38-42; Jan. 1996.

Strong et al.; Genotype and smoking history affect risk of levodopa-induced dyskinesias in parkinson's disease; Movement Disorders; 21(5); pp. 654-659; May 1, 2006.

Thiele et al. (Ed.); Oxidants and Antioxidants in Cutaneous Biology: Current Problems in Dermatology (Book 29); S. Karger; 196 pgs.; Feb. 2001.

Togasaki et al.; Dyskinesias in normal squirrel monkeys induced by nomifensine and levodopa; Neuropharmacology; 48(3); pp. 398-405; Mar. 31, 2005.

Togasaki et al.; Levodopa induces dyskinesias in normal squirrel monkeys; Annals of Neurology; 50(2); pp. 254-257; Aug. 1, 2001.

Togasaki et al.; The Webcam system: A simple, automated, computer-based video system for quantitative measurement of movement of nonhuman primates; Journal of Neuroscience Methods; 145(1); pp. 159-166; Jun. 30, 2005.

Tolosa et al.; Antagonism by piperidine of levodopa effects in Parkinson disease; Neurology; 27(9); pp. 875-877; Sep. 1, 1977.

U.S. Department of Health and Human Services, Food and Drug Administration, Center for Drug Evaluation and Research (CDER); Guidance for industry: Abuse-deterrent opioids-Evaluation and labeling; 24 pages; retrieved from the internet (http://www.fda.gov/downloads/drugs/guidancecomplainceregulatoryinformation/guidances/ucm344743.pdf); Jan. 2013.

United States of America VA/DoD; Tapering and discontinuing opioids; 2 pages; retrieved from the internet (http://www.healthquality.va.gov/guidelines/Pain/cot/OpioidTaperingFactSheet23May2013v1.pdf); on Sep. 1, 2016.

Vieregge et al.; Transdermal nicotine in PD: A randomized, double-blind, placebo-controlled study; Neurology; 57(6); pp. 1032-1035; Sep. 25, 2001.

Villafane et al.; Long-term nicotine administration can improve Parkinson's disease: report of a case after three years of treatment; Revista Neurologica Argentina; 27(2); pp. 95-97; (the year of publication is sufficiently earlier than the effective U.S. filing date and any foreign priority date so that the particular month of publication is not in issue) 2002.

Warburton et al.; Facilitation of learning and state dependency with nicotine; Psychopharmacology; 89(1); pp. 55-59; May 1, 1986.

(56)                    References Cited

OTHER PUBLICATIONS

Wermuth et al.; Glossary of terms used in medicinal chemistry Pure & Appl. Chem., vol. 70(5); 1129-1143; 1998 AC recommendations 1998); Pure and Applied Chemistry; 70(5); pp. 1129-1143; Jan. 1998.

Wesnes et al.; Effects of scopolamine and nicotine on human rapid information processing performance; Psychoparmacology; 82(3); pp. 147-150; Sep. 1, 1984.

Westman et al.; Oral nicotine solution for smoking cessation: a pilot tolerability study; Nicotine and Tobacco Research; 3(4); pp. 391-396; Nov. 1, 2001.

Wille et al.; cis-urocanic Acid Induces Mast Cell Degranulation and Release of Preformed TNF-alpha: A Possible Mechanism Linking UVB and cis-urocanic Acid to Immunosuppression of Contact Hypersensitivity; Skin Pharm Appl Skin Physiol; 12(1-2); pp. 18-27; Jan. 1999.

Wille et al.; Inhibition of irritation and contact hypersensitivity by ethacrynic acid; Skin Pharm Appl Skin Physiol; 11(4-5); pp. 279-288; Jul. 1998.

Wille et al.; Inhibition of Irritation and Contact Hypersensitivity by Phenoxyacetic Acid Methyl Ester in Mice; Skin Pharm Appl Skin Physiol; 13(2); pp. 65-74; Mar. 2000.

Wille et al.; Several different ion channel modulators abrogate contact hypersensitivity in mice; Skin Pharm Appl Skin Physiol; 12(1-2); pp. 12-17; Jan. 1999.

Wille, J.; Novel topical delivery system for plant derived hydrophobic anti-irritant active (presentation abstract No. 273); 226th ACS National Meeting; New York, NY; Sep. 7-11, 2003.

Wille; In Closing: an editorial on Plant-Derived Anti-irritants. Cosmetics & Toiletries, 118 (8), Aug. 2003.

Wille; Novel plant-derived anti-irritants; (presented Dec. 5-6, 2002 at the 2002 Ann. Scientific Mtg. & Tech. Showcase); J. Cosmet. Sci.; 54; pp. 106-107; Jan./Feb. 2003.

Wille; Thixogel: Novel topical delivery system for hydrophobic plant actives; in Rosen (Ed.) Delivery System Handbook for Personal Care and Cosmetic Products; 1st Ed.; ISBN: 978-0-8155-1504-3; pp. 762-794; Sep. 2005.

Youan; Chronopharmaceutics: gimmick or clinically relevant approach to drug delivery?; J Cont Rel; 98(3); pp. 337-353; Aug. 2004.

Yun et al.; A distributed memory MIMD multi-computer with reconfigurable custom computing capabilities; IEEE; Proc. Int'l. Conf. on Parallel and Distributed Systems; pp. 8-13, Dec. 10-13, 1997.

Zubieta et al.; Placebo effects mediated by endogenous opioid activity on mu-opioid receptors; 25(34); pp. 7754-7762; Aug. 24, 2005.

Johnston et al.; U.S. Appl. No. 18/662,905 entitled "Transdermal drug delivery devices and methods," filed May 13, 2024.

Netzel et al.; U.S. Appl. No. 18/673,223 entitled "Drug delivery methods and systems," filed May 23, 2024.

* cited by examiner

DRUG DELIVERY METHODS AND SYSTEMS

CROSS-REFERENCE TO RELATED APPLICATIONS

This application is a continuation of U.S. patent application Ser. No. 18/178,442, filed on Mar. 3, 2023, now U.S. Patent Application Publication No. 2024/0001095, which is a continuation of U.S. patent application Ser. No. 17/057, 318, filed Nov. 20, 2020, now U.S. Pat. No. 11,596,779, which is the U.S. National Stage Entry of International Patent Application No. PCT/US2019/034432, filed May 29, 2019, which claims priority to U.S. Provisional Patent Application No. 62/677,494, filed on May 29, 2018, the entirety of each are incorporated by reference herein.

This application may also be related to U.S. patent application Ser. No. 15/699,382, filed on Sep. 8, 2017, the entirety of which is incorporated by reference herein.

STATEMENT AS TO FEDERALLY SPONSORED RESEARCH

This invention was made with Government support under Contract No. 2R22CA171786-04 awarded by the National Institute of Health. The Government has certain rights in the invention.

INCORPORATION BY REFERENCE

All publications and patent applications mentioned in this specification are herein incorporated by reference in their entirety to the same extent as if each individual publication or patent application was specifically and individually indicated to be incorporated by reference.

BACKGROUND

Medicinal drugs are given to people to manage or improve their health for a variety of reasons, such as to prevent or treat a medical condition or disease such as diabetes, Parkinson's disease, ulcerative colitis, or to manage nicotine or another addiction or dependency, or to manage pain.

Some medicinal drugs are rapidly metabolized by the body. As a result, multiple doses of the drug over a period of time are often needed to provide a desired effect. In addition to having desired preventative or therapeutic effects, medicinal drugs can also have negative side-effects on the body that can range from irritating to life-threatening. Further, a person's body can develop tolerance to a drug, experience a diminished response to the drug after taking it for a period of time, and require higher doses to have an effect, resulting in increased drug use and additional side-effects. It is therefore beneficial to a person taking a drug to minimize the amount of drug he or she takes to prevent or minimize tolerance and other unwanted side-effects while still receiving the desired therapeutic effect from the drug.

Tobacco use (such as smoking) causes serious health problems and can lead to premature death. According to the United States Center for Disease Control (CDC), tobacco use causes more than 5 million deaths per year and contributes to the development of serious illnesses such as cancer, diabetes, heart disease, lung disease (bronchitis, chronic airway destruction, emphysema), and stroke. Despite anti-smoking advertising campaigns, legislation, taxation, and development of smoking cessation products to stop or prevent people from using tobacco, tobacco sales remains a multibillion dollar industry, generating an estimated $35 billion dollars per year in profits. Tobacco initially causes physical and mood-altering effects that are temporarily pleasing. Further, it is difficult for a person to stop using a tobacco product because tobacco contains nicotine. Nicotine is highly addictive, and not having the nicotine causes harsh withdrawal symptoms. It is very difficult for a person to overcome a nicotine addiction and stop smoking.

Medicinal drugs can be taken by tobacco users to help them overcome their nicotine addiction. Some products to help a person stop smoking contain small amounts of nicotine as a medicinal drug to minimize withdrawal symptoms and gradually wean a person from their nicotine addiction. Medicinal smoking cessation drugs such as nicotine have to be taken over an extended period of time (often over the course of many months) to give the body time to adjust to having less nicotine. Medicinal drugs, medical devices, and other products, including smoking cessation products, are regulated in the United States by the U.S. Food and Drug Administration (FDA). FDA approved products on the market to help a person quit smoking include various medicinal drugs that require a doctor's prescription as well as over-the-counter products. These products include capsules or tablets, gums, inhalers, lozenges, nasal sprays, and skin patches. These products have thus far been inadequate to get people to stop smoking: 68.9% of adult cigarette smokers say they want to stop smoking, and every year some 42.7% make an attempt to stop smoking, but are unsuccessful.

Existing smoking cessation products and other therapeutic and prophylactic treatments for health issues suffer from a variety of problems. They may be inconvenient or socially awkward to use. They may require careful and troublesome tracking of when they were used and how much was used to prevent overdosing. They may act too slowly after being administered and not produce a desired effect when it's needed. They may not be readily available when needed (such as while a person is sleeping). None have been wholly effective to for preventing or treating various medical or other conditions, and smoking remains a significant health and social problem.

Thus, new and improved drug delivery systems for bioactive agents, such as smoking cessation agents, are needed.

SUMMARY OF THE DISCLOSURE

In general, in one embodiment, a two-part bioactive agent delivery system includes a disposable part, a reusable part, and a solvent removal element. The disposable part includes an agent reservoir, a transdermal patch communicating with the agent reservoir and adapted to transdermally deliver the bioactive agent to a user. The transdermal patch has a bottom surface adapted to contact skin of the user, a top surface opposite the bottom surface, and a gas permeable membrane disposed over the top surface of the transdermal patch. The reusable part includes a power source and control electronics that are adapted to deliver bioactive agent dissolved in a solvent from the agent reservoir to the transdermal patch. The solvent removal element includes a gap disposed between the disposable part and the reusable part to create a flow path for gaseous solvent to flow from the gas permeable membrane to ambient air around the bioactive agent delivery system.

This and any other embodiments can include one or more of the following elements. The gap can extend between parallel features on the disposable part and the reusable part.

The gap can be formed when the disposable part and the reusable part are releasably engaged. The gap can be maintained with a spacer disposed between the disposable part and the reusable part. The spacer can extend from the disposable part. The spacer can extend from the reusable part. The system can further include at least one drainage port formed in an exterior surface of the reusable part or the disposable part. The disposable part can further include an agent outlet communicating with the agent reservoir and the transdermal patch. The agent outlet can be configured to provide the bioactive agent dissolved in the solvent to a space between the transdermal patch and the vapor permeable membrane. The agent reservoir can include a piston movably disposed in a chamber. The system can further include a spring extending between the agent reservoir piston and a surface to pressurize the agent reservoir when the spring is compressed and the agent reservoir contains a quantity of bioactive agent solution. The system can further include a bolus chamber communicating with the agent reservoir and an agent outlet, and the bolus chamber can include a piston movably disposed in a chamber. The volume of the bolus chamber can be less than the volume of the agent reservoir. The system can further include a valve having a first position communicating the agent reservoir with the bolus chamber and a second position communicating the bolus chamber with the agent outlet. The reusable part can include a valve driver, and the control electronics can be adapted to control the valve driver to actuate the valve to deliver bioactive agent solution from the agent reservoir to the bolus chamber and from the bolus chamber to the agent outlet. The system can further include a spring extending between the bolus chamber piston and a surface to pressurize the bolus chamber when the spring is compressed and the bolus chamber contains a quantity of bioactive agent solution. The system can further include a latch adapted to removably attach the disposable part to the reusable part. The latch can be positioned on one side of the system and a rail can be positioned along a second side of the system. The disposable part and the reusable part can be configured to slide relative to one another along the rail until the latch is activated to attach the disposable part to the reusable part. The system can further include a connection detector adapted to detect a connection between the disposable part and the reusable part. The connection detector can include a magnet. The magnet can be disposed in the disposable part. The magnet can be disposed in the reusable part. The connection detector further can include a magnetoresistive switch.

In general, in one embodiment, a method of delivering bioactive agent includes: connecting a reusable part of a delivery system to a disposable part of the delivery system to form a flow path between the reusable part and the disposable part, delivering the bioactive agent dissolved in a solvent from a reservoir of the disposable part to a transdermal membrane of the disposable part, and allowing the solvent to evaporate and flow from the transdermal membrane through a gas permeable membrane and along the flow path to ambient air around the delivery system.

This and any other embodiments can include one or more of the following elements. The method can further include applying the transdermal membrane to skin of a user. The method can further include delivering the bioactive agent to the skin. The delivering step can include controlling with the reusable part movement of the bioactive agent dissolved in the solvent from the reservoir to the transdermal membrane. The controlling step can include actuating a valve. The method can further include detecting a connection between the disposable part and the reusable part. The detecting step can include sensing a magnetic field.

BRIEF DESCRIPTION OF THE DRAWINGS

The novel features of the invention are set forth with particularity in the claims that follow. A better understanding of the features and advantages of the present invention will be obtained by reference to the following detailed description that sets forth illustrative embodiments, in which the principles of the invention are utilized, and the accompanying drawings of which:

Figures 19A, 19B, 19C:
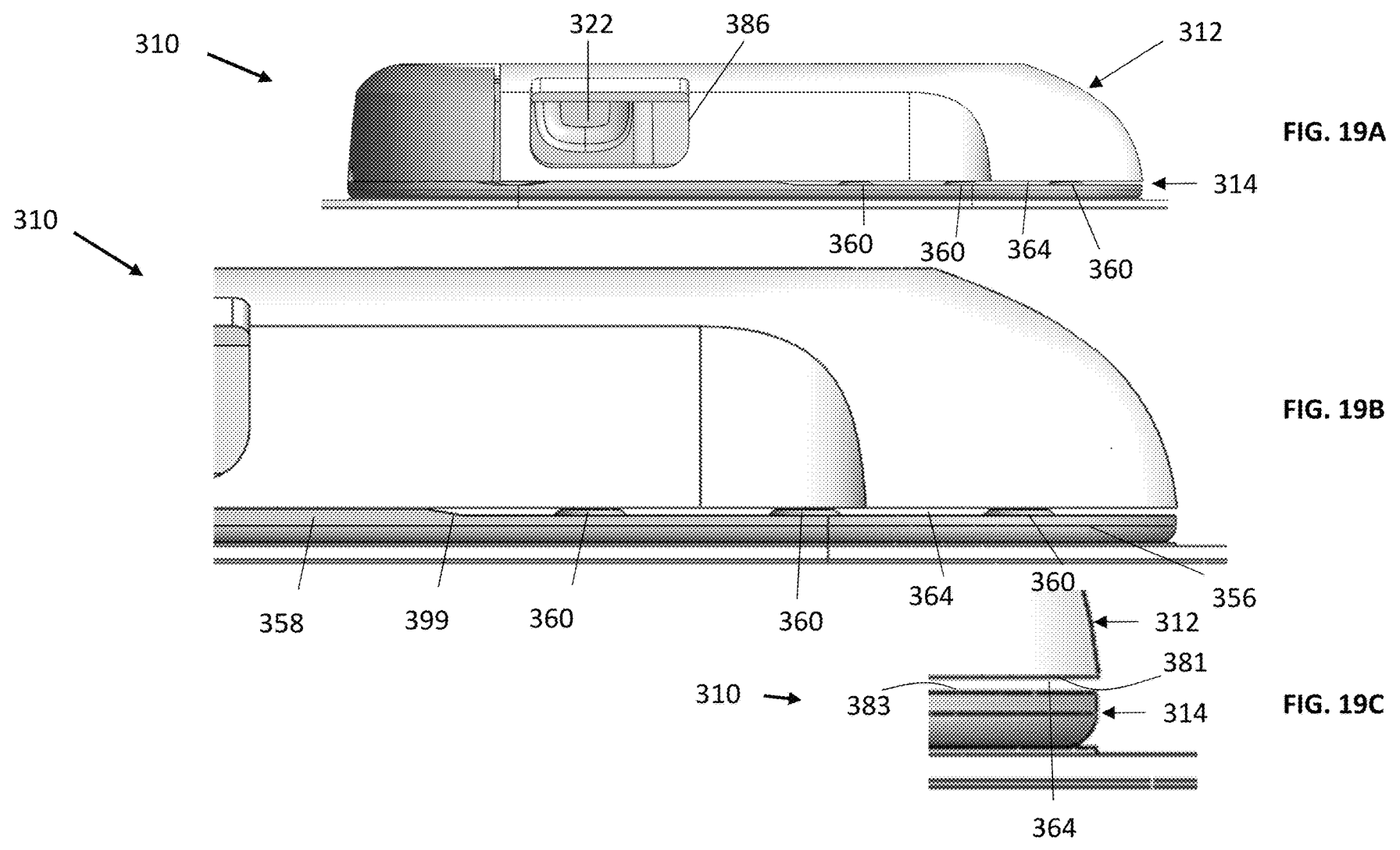

FIGS. 19A-19C are side view of the two-part bioactive agent delivery system of FIG. 9.

FIGS. 20A-20C are perspective views of the disposable part of the two-part bioactive agent delivery system of FIG. 9.

DETAILED DESCRIPTION

Figures 1, 2, 3:
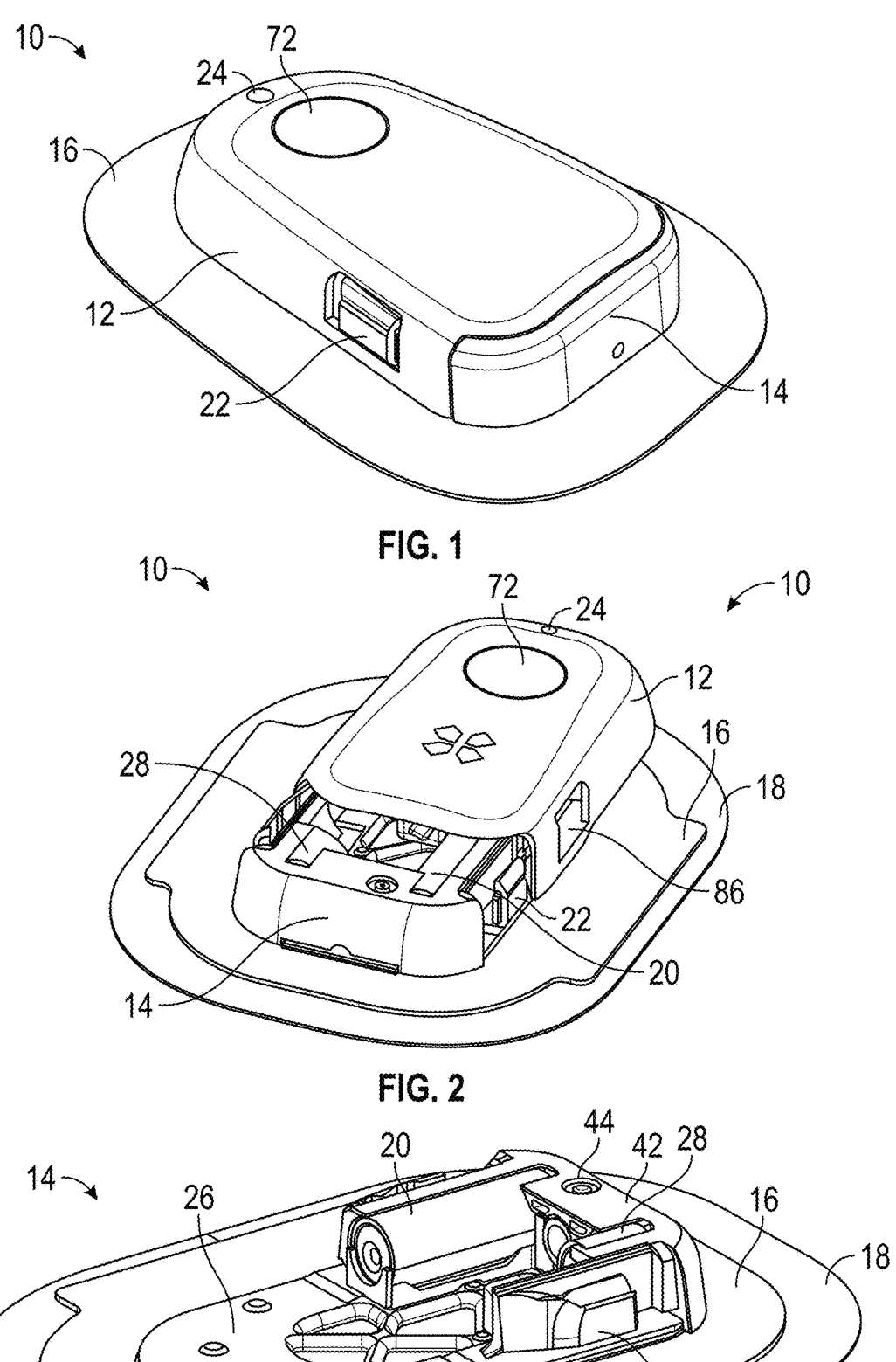
FIG. 1 is a perspective view of a two-part bioactive agent delivery system according to an embodiment.
FIG. 2 is a perspective view of a partially connected two-part bioactive agent delivery system according to an embodiment.
FIG. 3 is a perspective view of a portion of the disposable part of the two-part bioactive agent delivery system of FIG. 1 or FIG. 2.

Described herein are systems and methods for delivering bioactive agents. The systems can include two parts: a disposable part and a reusable part. The disposable part may include bioactive agent and system parts that come into contact with bioactive agent, and the reusable part may not contain bioactive agent and system parts that come into contact with bioactive agent.

In some embodiments, the disposable part can include an agent reservoir, a bolus chamber, a valve alternately communicating the reservoir with the bolus chamber and the bolus chamber with an outlet, a solvent removal element, and a transdermal membrane receiving the agent from the outlet. The reusable part can include a valve driver and control electronics.

These bioactive agent delivery systems described herein can deliver a solution of the bioactive agent to a transdermal patch. Solvent from the bioactive agent solution can evaporate from the transdermal patch through the solvent removal element (e.g., a gap between the reusable part and the disposable part) to control the manner in which the bioactive agent passes from the patch into the user's skin.

A bioactive agent delivery system as described herein may be useful for delivering a bioactive agent to any part on or in a user's body. In some particular variations, a bioactive agent delivery system as described herein may be especially useful for delivering a bioactive agent topically or transdermally to or through a user's skin to a skin layer or bloodstream. Effective topical or transdermally delivery may be aided by use of a skin delivery membrane such as described herein for transferring active agent across the skin that is fully or sufficiently wetted to effectively transfer a dose of bioactive agent to a user's skin. In some variations, a bioactive agent delivery system may be electronically controlled, programmable, portable, and/or wearable.

The bioactive agent delivery systems described herein may reproducibly deliver a fixed amount of a bioactive agent to a user, such as to a user's skin, to have a therapeutic or prophylactic effect on the user. In some variations, the bioactive agent delivery systems may be configured to be wearable and to deliver a fixed amount of a bioactive agent to a user's skin in a relatively thin, quiet, easy to use, convenient, electronically controlled system. The bioactive agent delivery systems may be configured to be attached to a user's body (such as for a day or shorter or longer), connect with a user's skin, and deliver a bioactive agent across the user's skin.

The bioactive agent delivery systems as described herein may be useful for delivering a bioactive agent to a user for addiction or dependency management or prevention such as for a drug addiction, for diabetes or other disease management or prevention, for pain management or prevention, or for another therapeutic or prophylactic purpose. The systems, devices, and methods may be especially useful for delivering multiple doses of a drug or other bioactive agent to a user over time with a safe, inexpensive, convenient, and easy-to-use system that minimizes risk of a drug or other bioactive agent overdose.

A bioactive agent delivery system as described herein may be configured to deliver multiple doses or boluses during the course of a day and/or for multiple days. Delivering multiple boluses may be especially useful to help a user control cravings or other withdrawal symptoms by delivering a bioactive agent dose (e.g., a dose of nicotine) especially during (or before) a time of day when cravings or withdrawal symptoms are normally most troublesome (such as delivering a dose during the night to prevent cravings upon waking).

Further, having a bioactive agent delivery system with a disposable part may allow the system to be relatively small or flat and easy to wear. For example, a system may be relatively small or flat because the disposable part needs only contain a limited amount of bioactive agent and/or the reusable part needs only be imparted with sufficient force or power for a limited number of dose deliveries before being recharged. In some examples, a bioactive delivery system as described herein may be less than about 20 mm, less than about 16 mm, less than about 15 mm, less than about 14 mm, less than about 13 mm, less than about 12 mm, less than about 11 mm or less than about 10 mm in thickness and may be less than 40 mm, less than 35 mm in length or width, or less than 30 mm in length or width. In some examples, a system may have less than 1500 mm$^2$ or less than 1000 mm$^2$ top (or bottom) surface area. "Bottom" in this context generally refers the part(s) of the system closest to a user. If a system includes a transdermal patch, bottom may refer to the transdermal patch and to the skin delivery member of a transdermal patch. A surface area of one side of a skin delivery member may be at least 100 mm$^2$, at least 500 mm$^2$, at least 1500 mm$^2$, at least 2000 mm$^2$, at least 2500 mm$^2$ at least 3000 mm$^2$ or less than or between any of these numbers (such as at least 500 mm$^2$ and less than 2000 mm$^2$).

Figures 4, 5:
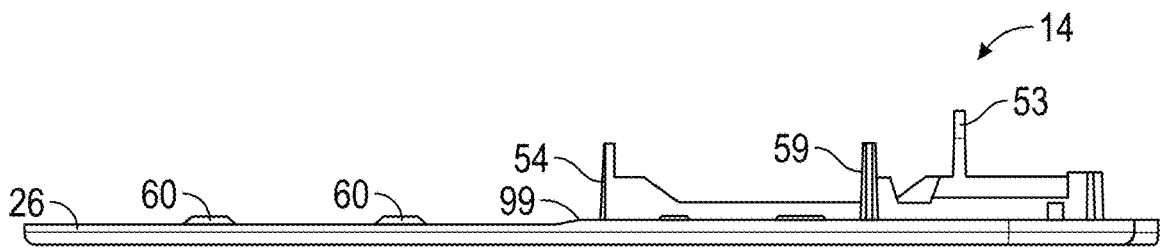
FIG. 4 is an exploded view of the disposable part of the two-part bioactive agent delivery system of FIG. 1 or FIG. 2.
FIG. 5 is a side view of a chassis of the disposable part of the two-part bioactive agent delivery system of FIG. 1 or FIG. 2.

FIGS. 1 and 2 show a two-part bioactive agent delivery system according to an embodiment of this invention. The system 10 has a reusable part 12 connectable to a disposable part 14. An adhesive element 16 (such as, e.g., adhesive foam) extends around the periphery of the disposable part 14, and a removable release liner 18 covers the adhesive surface of the adhesive element 16. The disposable part 14 also has a reservoir 20 containing a solution of the bioactive agent (e.g., nicotine) to be delivered transdermally to user. The reusable part 12 has control electronics, a user interface button 72, and an LED mode status indicator 24. One or more latches 22 may be used to connect and disconnect the disposable part 14 from the reusable part 12. An outer surface of the bioactive agent delivery system 10 when the reusable part 12 and the disposable part 14 are connected together may have any shape, such as circular, ovoid, rectangular, square, and may be contoured (or able to be contoured) to better fit a user's skin Further details of the disposable part 14 are shown in FIGS. 3-5. Mounted on a chassis 26 are the reservoir 20, a bolus chamber 28, and a valve chamber 30. A manifold communicates the reservoir 20 with the valve chamber 30 and the valve chamber 30 with the bolus chamber 28. Movable pistons 32 and 34 are disposed in the reservoir 20 and bolus chamber 28, respectively. A rotatable valve element 36 is disposed in valve chamber 30.

Attached to the underside of chassis 26 (e.g., by heat bonding) are a gas permeable membrane 38 (formed, e.g., from Poreflon® polytetrafluoroethylene) and a transdermal drug delivery patch 40 (e.g., a Celgard® membrane). An upper housing 42 supports latch(es) 22 and partially covers reservoir 20, valve chamber 30, bolus chamber 28, and chassis 26. An opening 44 in housing 42 leads to a fill port 46 that can be used to add a solution of the bioactive agent to reservoir 20 and bolus chamber 28. A fill port plug 48 seals fill port 46 after filling the reservoir and bolus chamber with a solution of the bioactive agent.

Chassis 26 has supports 53, 54, and 59 engaging the reservoir 20, valve chamber 30, and bolus chamber 28, respectively, to hold the reservoir 20, valve chamber 30, and bolus chamber 28 in place. One or more raised spacers 60 extend upwardly from the top side of chassis 26. Open vents 62 in chassis 26 are disposed over the gas permeable membrane 38. Spacers 60 engage the underside of the reusable part 12 to establish a gap 64 forming a flow path for evaporated solvent passing from transdermal patch 40 through gas permeable membrane 38 and chassis vents 62, as described below. In an alternative embodiment, the one or more spacers 60 may extend from the reusable part instead of, or in addition to, the spacer(s) extending from the disposable part. Ramped ledges 99 can transition the chassis from a thinner section 56 to a thicker section 58.

Figures 6, 7:
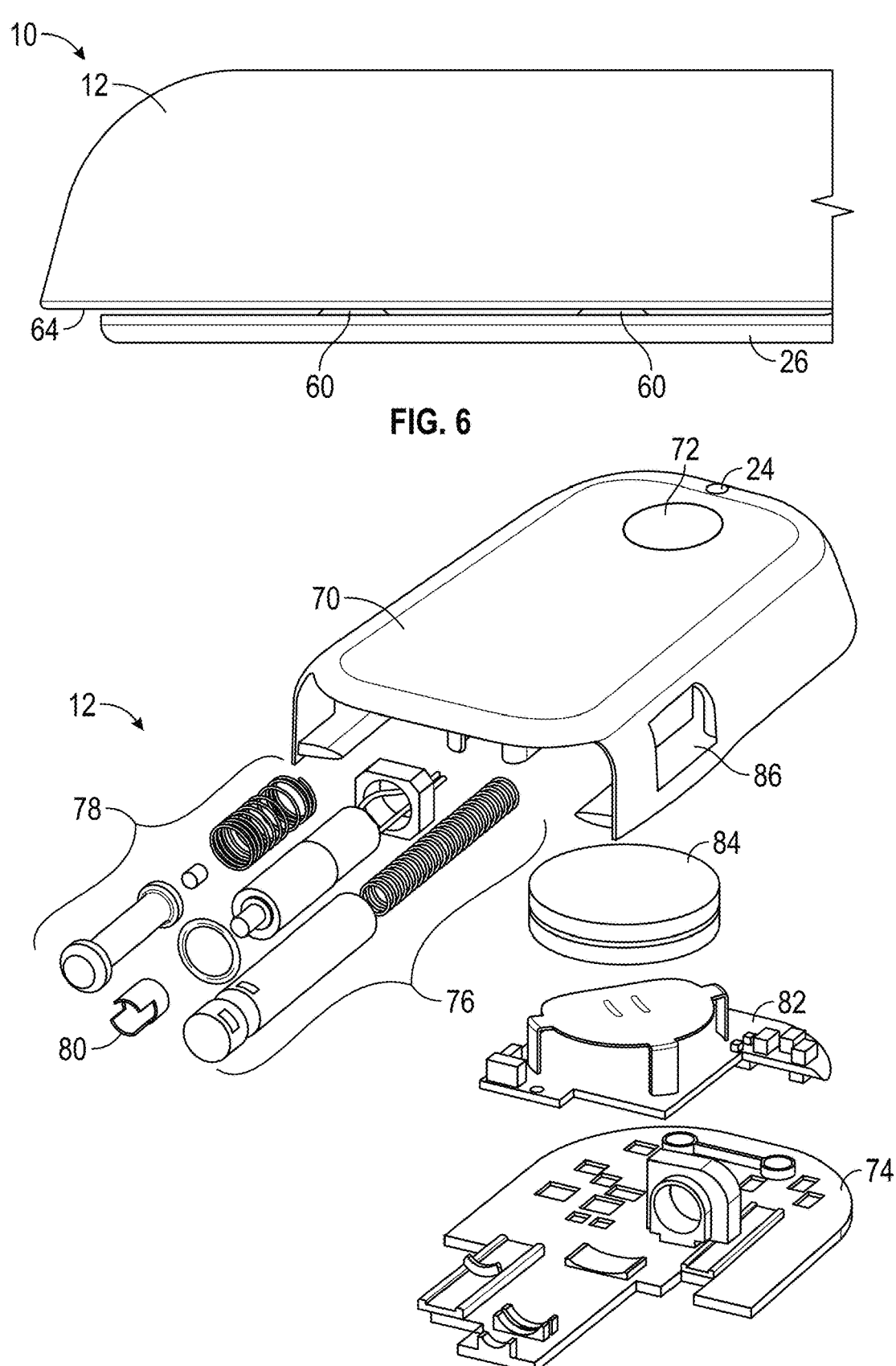
FIG. 6 is a side view of the two-part bioactive agent delivery system of FIG. 1 or FIG. 2.
FIG. 7 is an exploded view of the reusable part of the two-part bioactive agent delivery system of FIG. 1 or FIG. 2.

FIG. 7 shows components of the reusable part 12. A latch element 86 adapted to engage with the latch 22 of the disposable part is formed in an upper housing 70. Disposed between an upper housing 70 and a lower housing 74 are a spring assembly 76 for the reservoir 20 and a spring assembly 78 for the bolus chamber 28. When the disposable part 14 is engaged and latched with the reusable part 12, the spring assemblies 76 and 78 engage with the pistons 32 and 34, respectively, and the springs of the spring assemblies 76, 78 compress to pressurize the bioactive agent solution in reservoir 20 and bolus chamber 28, respectively. A motor assembly 80 engages valve element 36 and operates under the control of a microprocessor on the printed circuit board 82 using power from battery 84 to turn valve element 36 between a position in which reservoir 20 communicates with bolus chamber 28 and a position in which bolus chamber 28 communicates with patch 40. A control button 72 in the upper housing 70 communicates with the microprocessor. The control button 72 can further serve as a user input mechanism. It may be depressed, e.g., to power on the electronics; to pair the device with a smartphone application; to provide information about the user, such as the experience of a craving for a cigarette; or to request a device status update or other information. Status indicator 24 can indicate the status of the system, e.g., whether the system is delivering fluid, in stand-by mode, or empty of bioactive agent.

The system 10 may be used to deliver a bioactive agent transdermally to a user. Disposable part 14 may be prefilled with a solution of the bioactive agent. The disposable part 14 may be connected to the reusable part 12 and latched with latch components 22 and 86. This connection compresses spring assemblies 76 and 78 against pistons 32 and 34 of reservoir 20 and bolus chamber 28, respectively, to pressurize the bioactive agent solution in the reservoir 20 and bolus chamber 28. Release liner 18 may be removed so that the adhesive on the underside of adhesive element 16 can be attached to the user's skin. In response to a signal from the device's microprocessor, motor assembly 80 turns rotatable valve element 36 to a position in which the contents of bolus chamber 28 are delivered through an agent outlet in chassis 26 to a space between gas permeable membrane 38 and transdermal patch 40. As the bioactive agent moves from the patch 40 into the user's skin, solvent from the bioactive agent solution evaporates and passes through gas permeable membrane 38 and the vents 62 in chassis 26 to reach the flow path defined by gap 64. Removal of solvent from the transdermal patch 40 enables the percentage of bioactive agent in liquid solution in the patch to remain high enough to maintain a desired transdermal delivery rate of the bioactive agent until essentially all of the bioactive agent in the bolus of bioactive agent solution has been delivered. Subsequent boluses of bioactive agent may be delivered by actuating the valve element 36 to enable refilling of the bolus chamber 28 with solution from the reservoir 20 followed by movement of the valve element 36 to permit delivery of the next bolus from bolus chamber 28 to the transdermal patch 40. The timing of the bolus deliveries are under the control of the programmed microprocessor.

Further details of the operation of the reusable and disposable parts and components, including reservoir 20, bolus chamber 28, and valve 36 and/or the control button 72 and indicator 24, to deliver the bioactive agent solution to the transdermal patch at controlled times may be found in US Publication No. 2016/0220798, the entirety of which is incorporated by reference.

Figure 8:
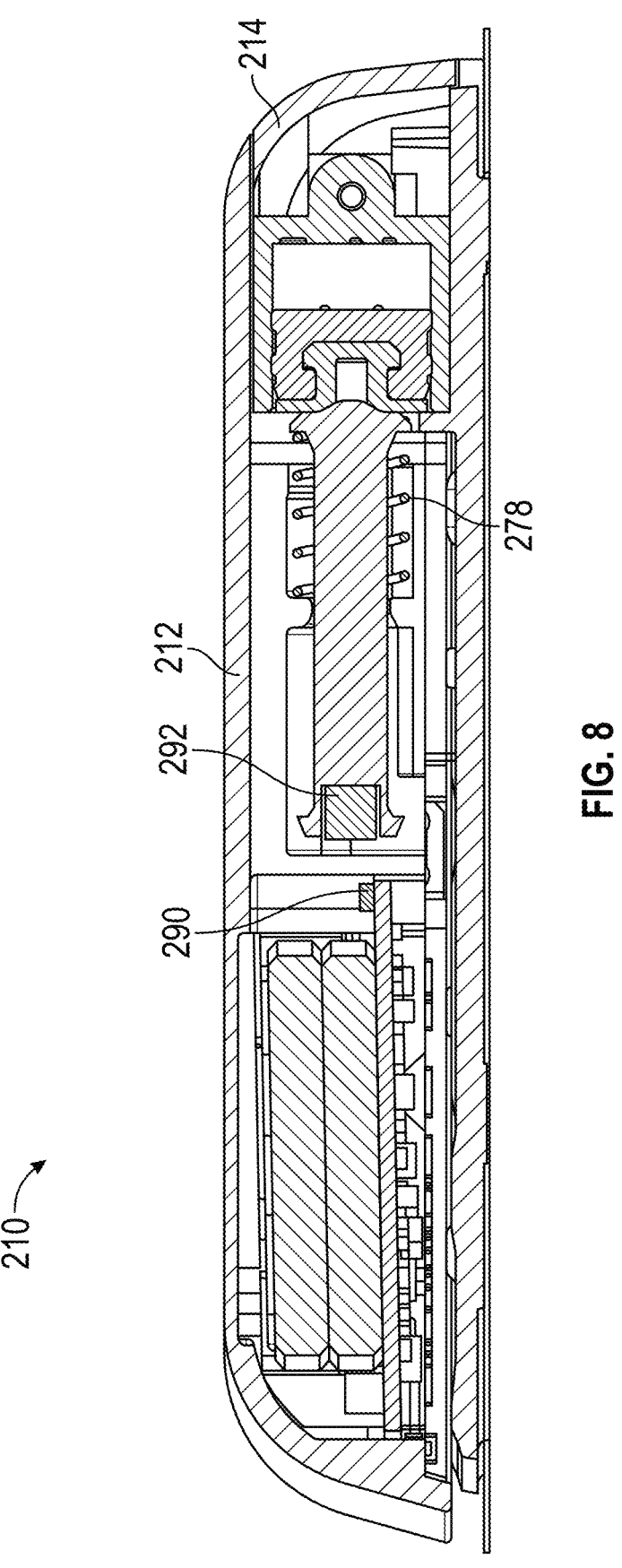
FIG. 8 shows a connection sensor for a two-part bioactive agent delivery system according to an embodiment.

In some embodiments, the systems described herein can include a sensor to detect connection of a disposable part with the reusable part. In one embodiment shown in FIG. 8, a system 210 includes a magnetoresistive switch 290 disposed in the reusable part 212 that detects a magnet 292 disposed in the spring assembly 278. In an alternative embodiment, the magnet can be disposed in the disposable part 214 (see, for example, magnet 392 in FIG. 21B). Use of the magnetoresistive switch 290 enables the electronics to be encapsulated and waterproof. In some embodiments, a reed switch or a Hall sensor may be used as an alternative to the magnetoresistive switch. Information about the connection times and durations of the reusable part with the disposable part may be used, e.g., to monitor compliance with a drug delivery regimen.

Figures 9, 10:
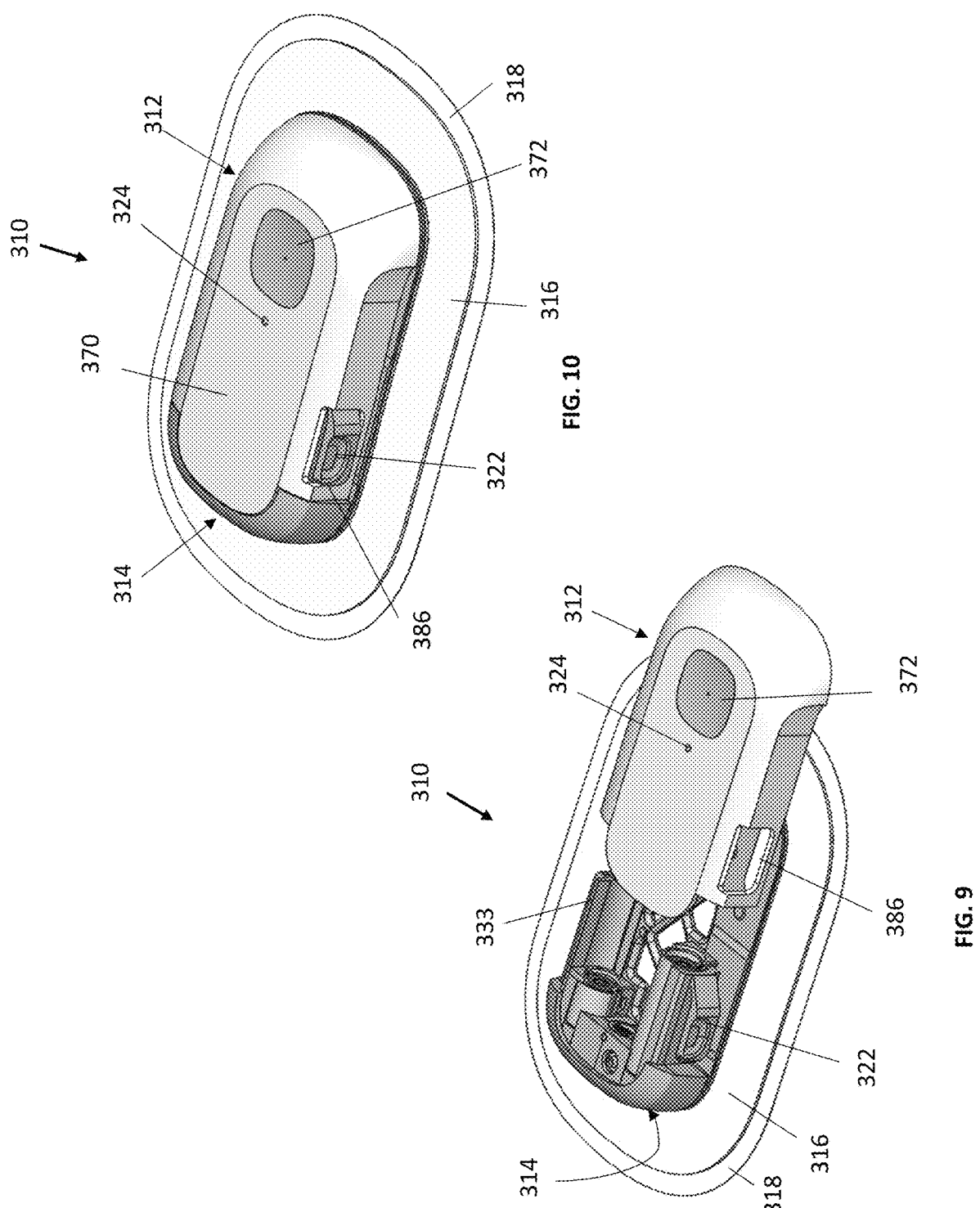
FIG. 9 is a perspective view of a partially connected two-part bioactive agent delivery system according to an embodiment.
FIG. 10 is a perspective view of the two-part bioactive agent delivery system of FIG. 9.
Figures 11, 12, 13:
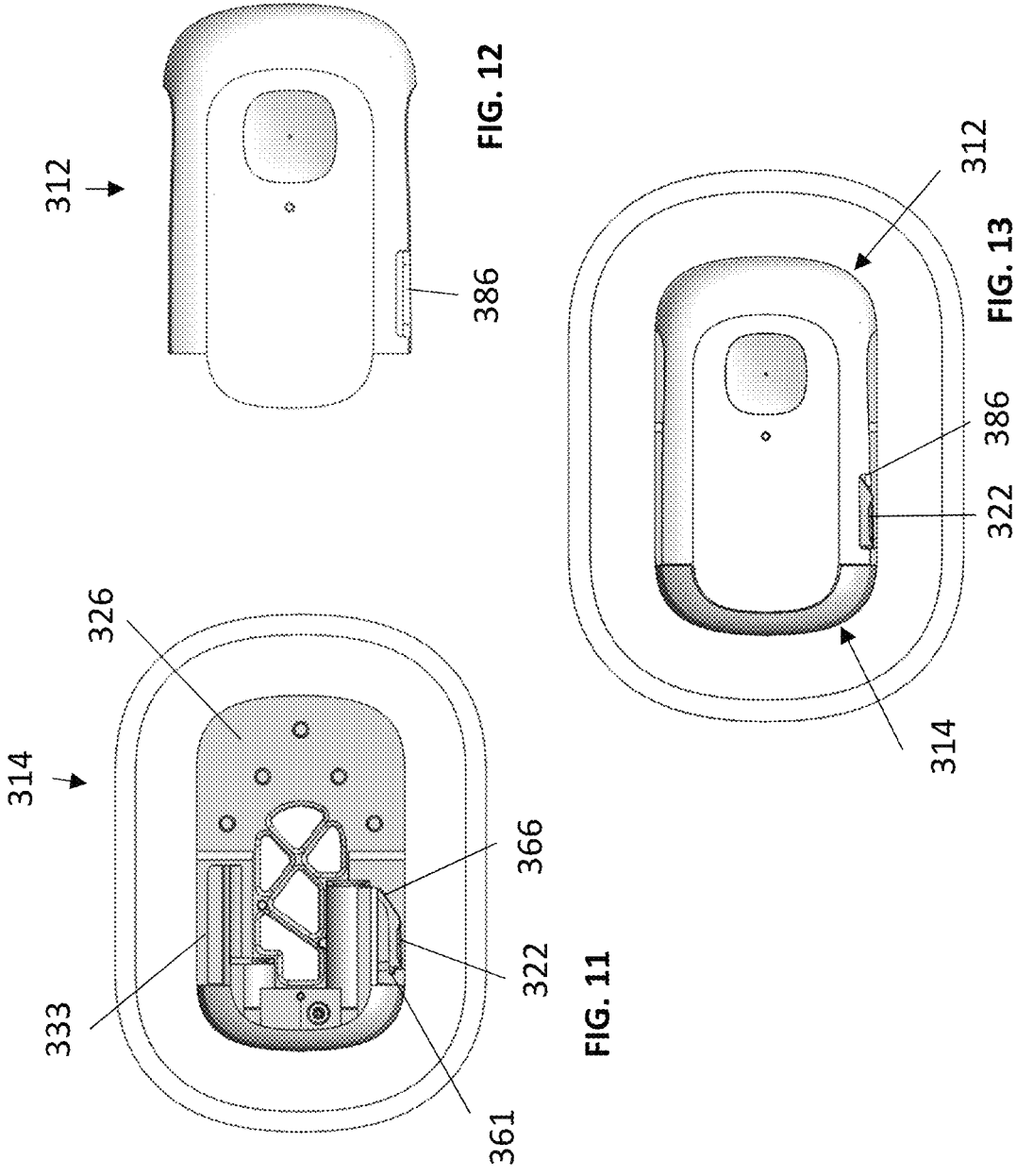
FIG. 11 is a top view of the disposable part of the two-part bioactive agent delivery system of FIG. 9.
FIG. 12 is a top view of the reusable part of the two-part bioactive agent delivery system of FIG. 9.
FIG. 13 is a top view of the two-part bioactive agent delivery system of FIG. 9.
Figures 14, 15, 16:
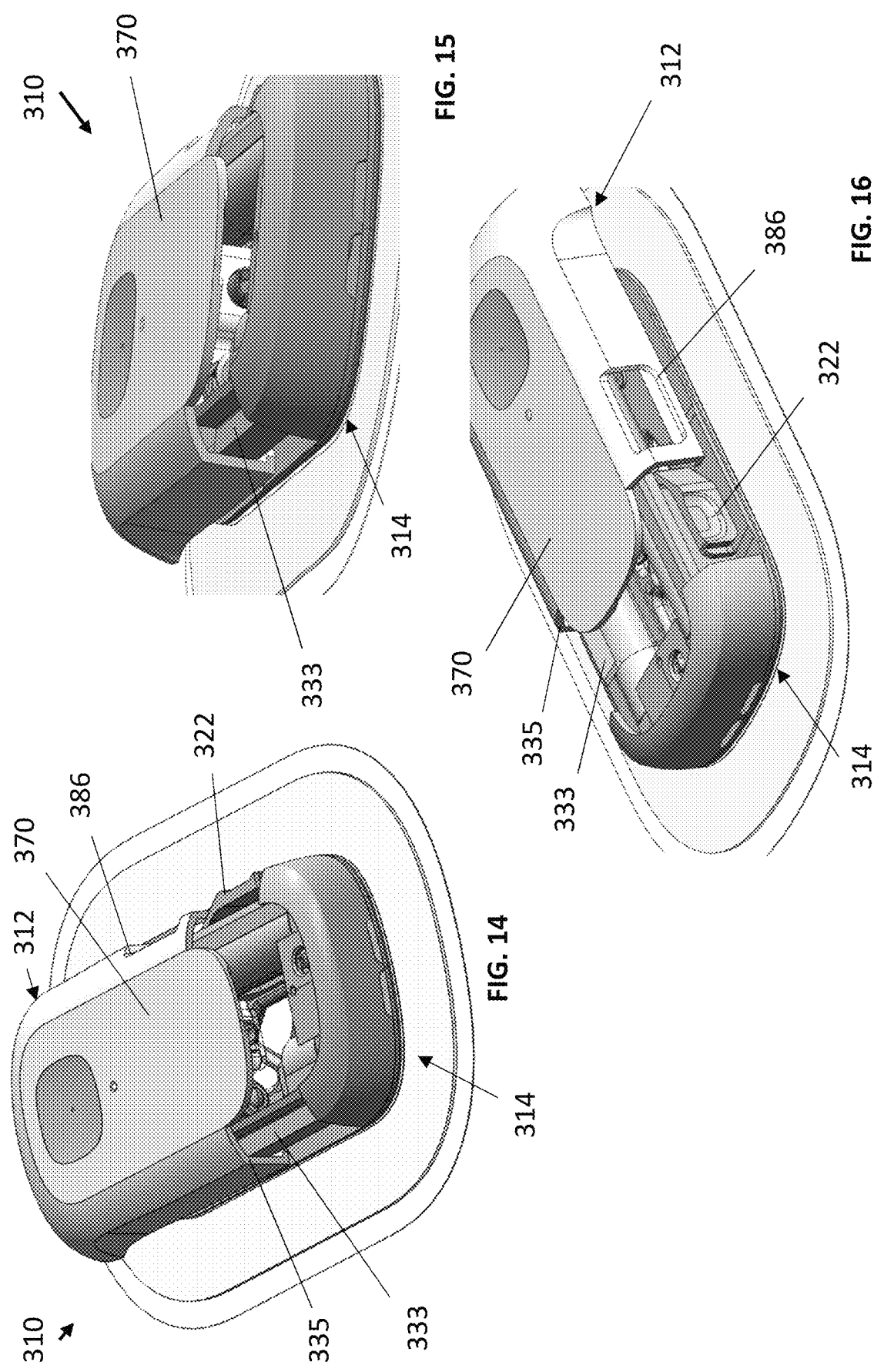
FIGS. 14-16 are additional perspective views of the partially connected two-part bioactive agent delivery system of FIG. 9.
Figure 17:
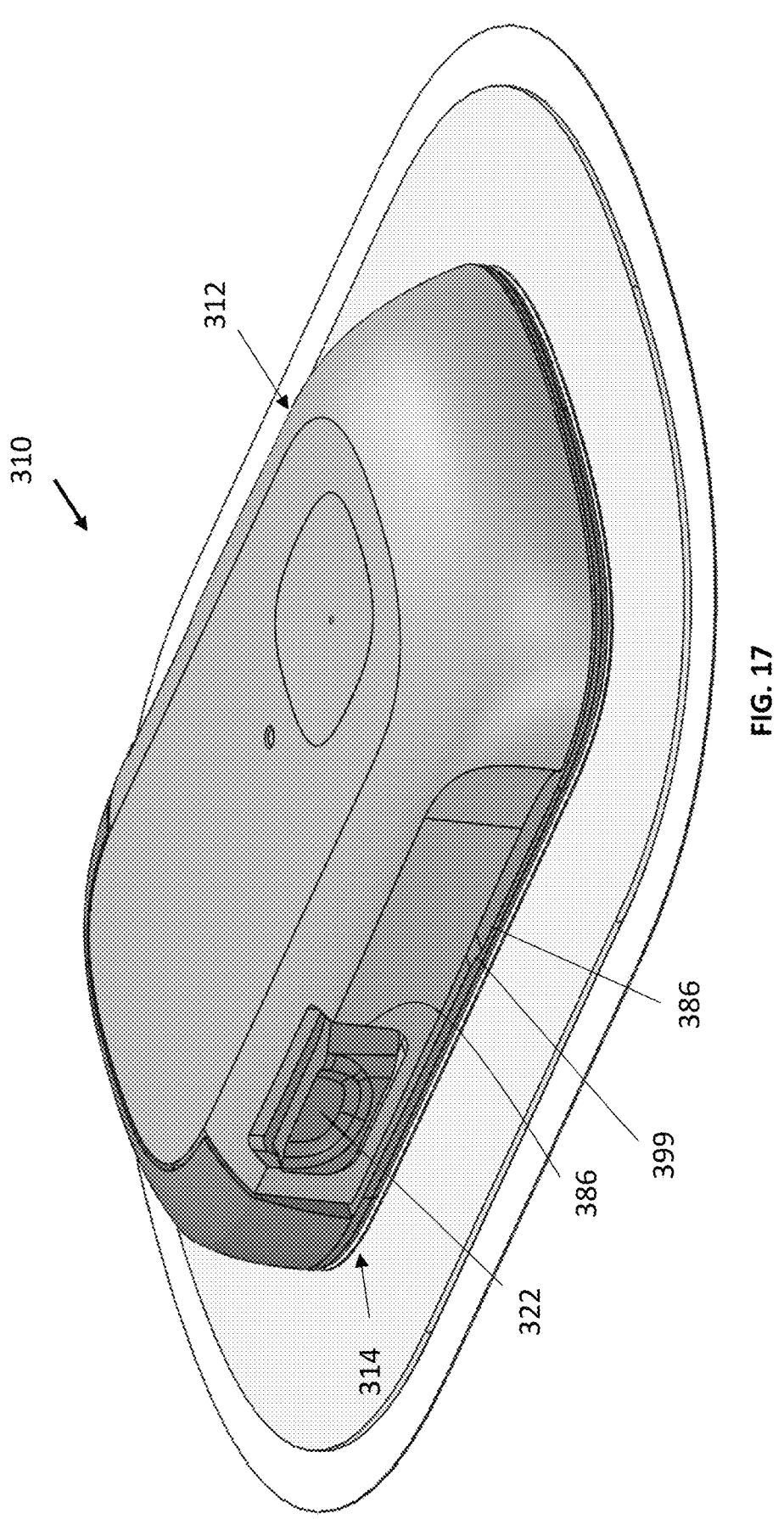
FIG. 17 is another perspective view of the two-part bioactive agent delivery system of FIG. 9.
Figure 18:
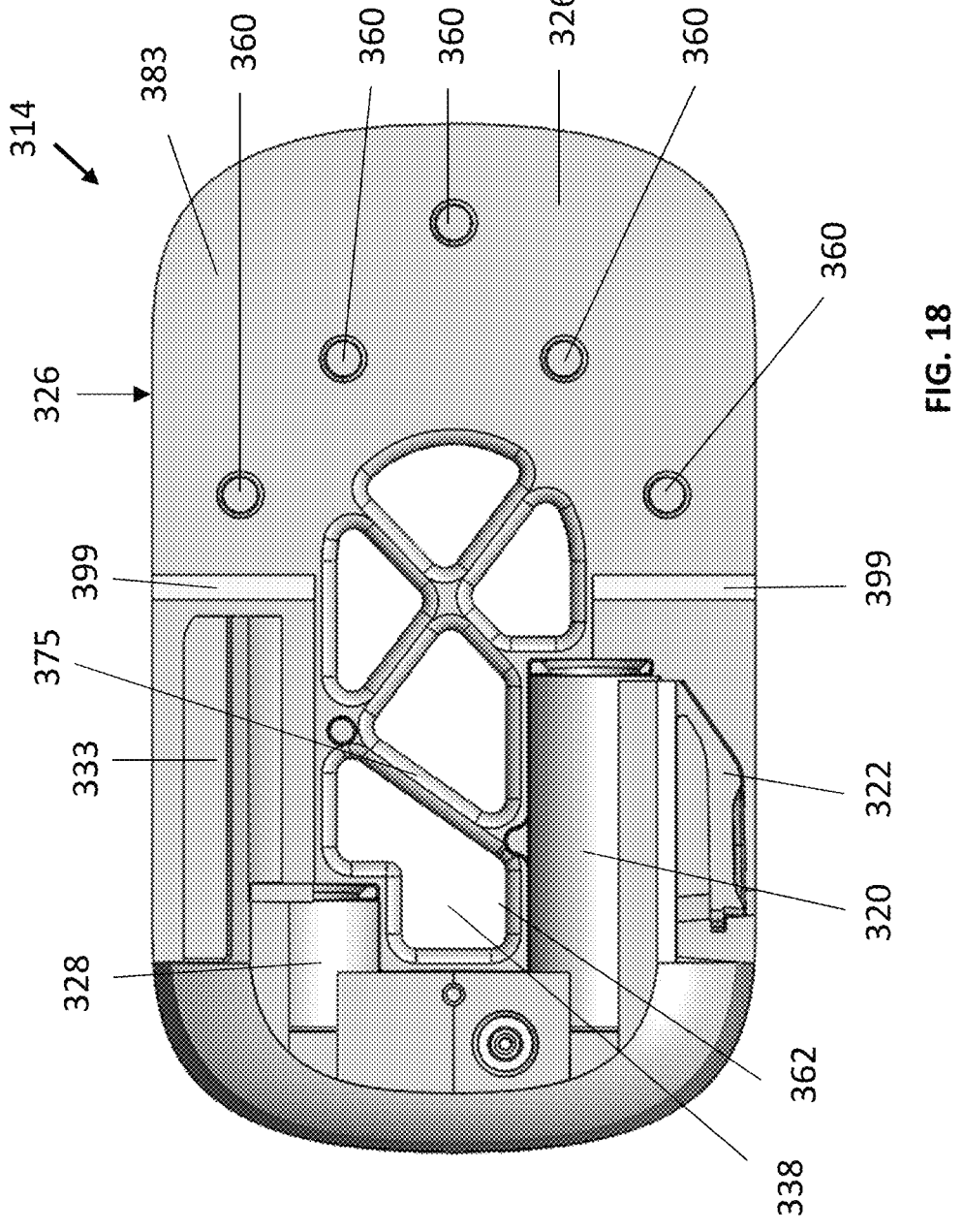
FIG. 18 is a top view of the chassis of the two-part bioactive agent delivery system of FIG. 9.

Another exemplary two-part bioactive agent delivery system 310 that is similar to system 10 is shown in FIGS. 9-22. Referring to FIGS. 9-10, system 310 includes a reusable part 312 connectable to a disposable part 314, an adhesive element 316, and release liner 318. The reusable part 312 has control electronics, a user interface button 372, and an LED mode status indicator 324. When the reusable part 312 and the disposable part 314 are connected together, the upper housing 342 of the disposable part 314 and the housing 370 of the reusable part abut one another to create a substantially smooth outer contour.

As shown in FIGS. 11-16, the system 310 further includes a single latch 322 and rail 333 to connect and disconnect the disposable part 314 from the reusable part 312. The latch 322 can be on a first side of the disposable part 314 while the rail 333 can be positioned on a second opposite side of the disposable part 314. The rail 333 can extend substantially parallel with the longitudinal axis of the system 310. Further, the rail 333 can be configured to mate with a sliding element 335 (e.g., a c-shaped element) on the housing 730 of the reusable part 312. In use, the sliding element 335 can slide along the rail 333 as the disposable part 314 and reusable part 312 are engaged. The rail 333 can thus advantageously ensure that the disposable part 314 and reusable part 312 remain aligned as they are connected or disconnected. The latch 322 can have a cantilevered first end 361 and a sloped or ramped second end 366 (see FIG. 11). The ramped second end 366 can be connected to the upper housing 342 of the disposable part 314 while the cantilevered first end 361 can be configured to mate with a latch element 386 (e.g., an opening) on the housing 370 of the reusable part 312. The latch 322 and latch element 386 can function to hold the disposable part 314 and reusable part 312 together until the latch 322 is depressed by the user.

Referring to FIGS. 17-19C, the system 310 can include open vents 362 through the chassis 326 so as to expose the membrane 338 thereunder. The vents 362 can be positioned in a central portion of the chassis 326 and can be cut so as to maximize the exposure of the surface of the membrane 338. For example, the vents 362 can expose 5-30% of the surface of the membrane 338, such as 10-20% of the surface. Diagonal struts 375 can extend between the vents 362 to maintain the strength of the chassis 362. The vents 326 can connect to gap 364 between the reusable part 312 and the disposable part 314. The gap 364 can be formed between the parallel bottom surface 381 of the reusable part 312 and top surface 383 of the disposable part 314. The gap 364 can be formed by the framework of the system, including the mating between the rail 333 and sliding element 335 and the mating between the latch 322 and latch element 382. Additionally, one or more spacers 360 can be configured to help maintain the gap 364. The spacers 360 can be, for example, cylindrical or semi-spherical elements that protrude upwards (i.e., from the top surface 383 of) the chassis 326. Further, the spacers 360 can be positioned on a side of the chassis 360 that is opposite to the reservoir 320, bolus chamber 320, and valve chamber 330 (e.g., on the thinner section 356). There can be a plurality of spacers 360, such as 3-5 spacers 360, that are substantially equally spaced around the vents 362. Each of the spacers 360 can have a small diameter (e.g., a diameter that is less than 10% of the width of the chassis 26). Additionally, ramped ledges 399 can transition between the thinner section 356 of the chassis 326 and the thicker section 358 of the chassis 326. In some embodiments, there can be two ledges 399 that are axially aligned with one another at approximately the center of the chassis 326.

The spacers 360 can engage the bottom surface 381 of the reusable part 312 to maintain the gap 364 and therefore to form a flow path for evaporated solvent passing through the vents 362. In an alternative embodiment, the one or more spacers may extend from the reusable part instead of, or in addition to, the spacers extending from the disposable part. Additionally, the thick section 358 of the chassis 326 can engage the bottom surface 381 of the reusable part 312 (i.e., can be coincident with the bottom of the reusable part 312), which can further maintain the gap 364 above the thin section 356.

Figures 20A, 20B, 20C:
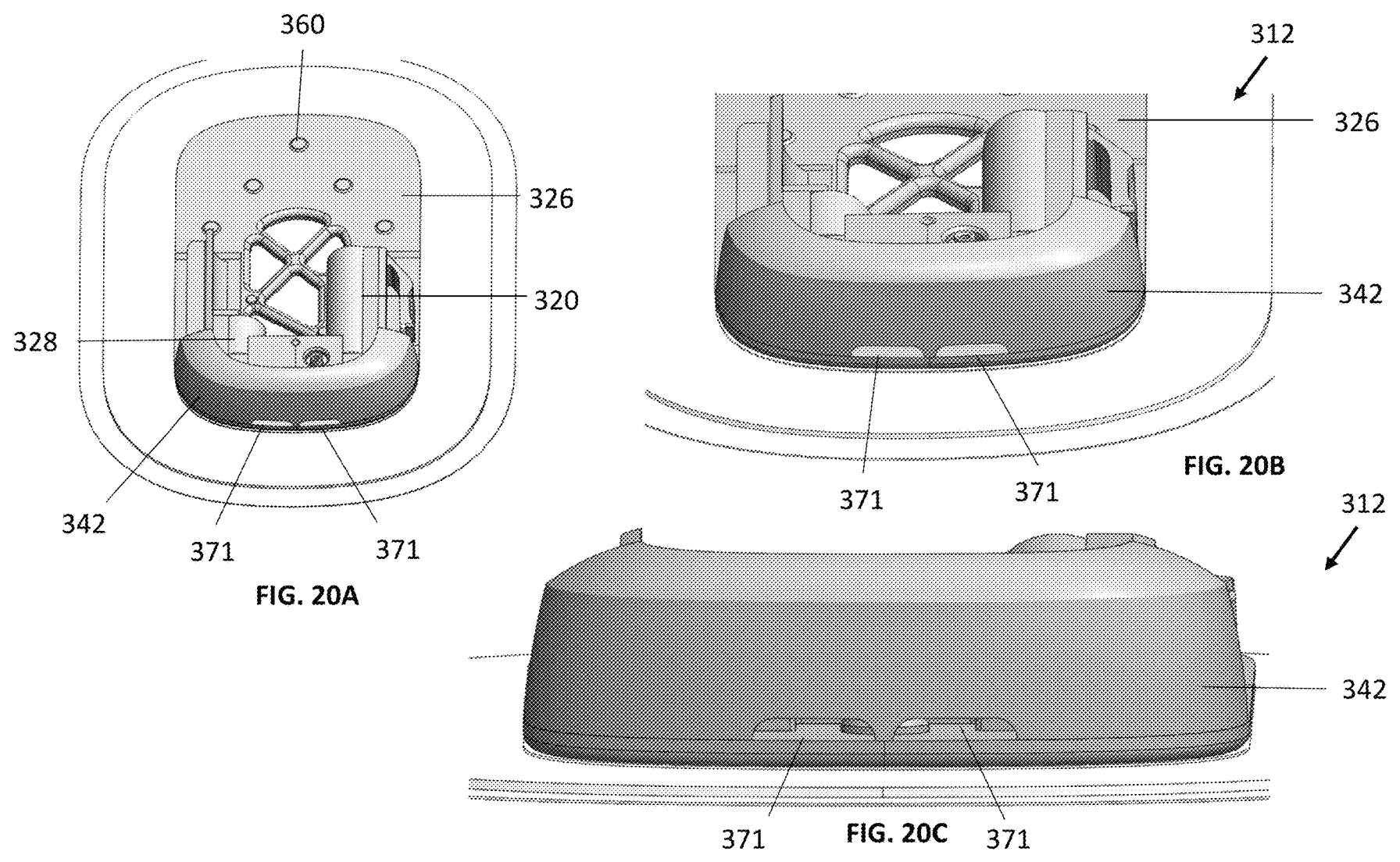

Referring to FIGS. 20A-20C, the system 310 can further include one or more drainage ports 371 therein that are aligned with or connected with the gap 364 and can provide drainage for any excess fluid left in the side of the system 310. The drainage ports 371 can be formed in the upper housing 377 of the disposable part 312 proximate to the thicker section 358 of the chassis 326 and can facilitate water drainage (e.g., from the user bathing and/or otherwise getting fluid in or on the system 310). In some embodiments, the drainage ports 371 can be positioned such that, when the system is worn on the body (e.g., on the arm) and the device 310 is turned vertically, water will exit the device by gravity via ports 371. The ports 371 can be sized so as to avoid capillary pooling of water therein.

Figure 21B:
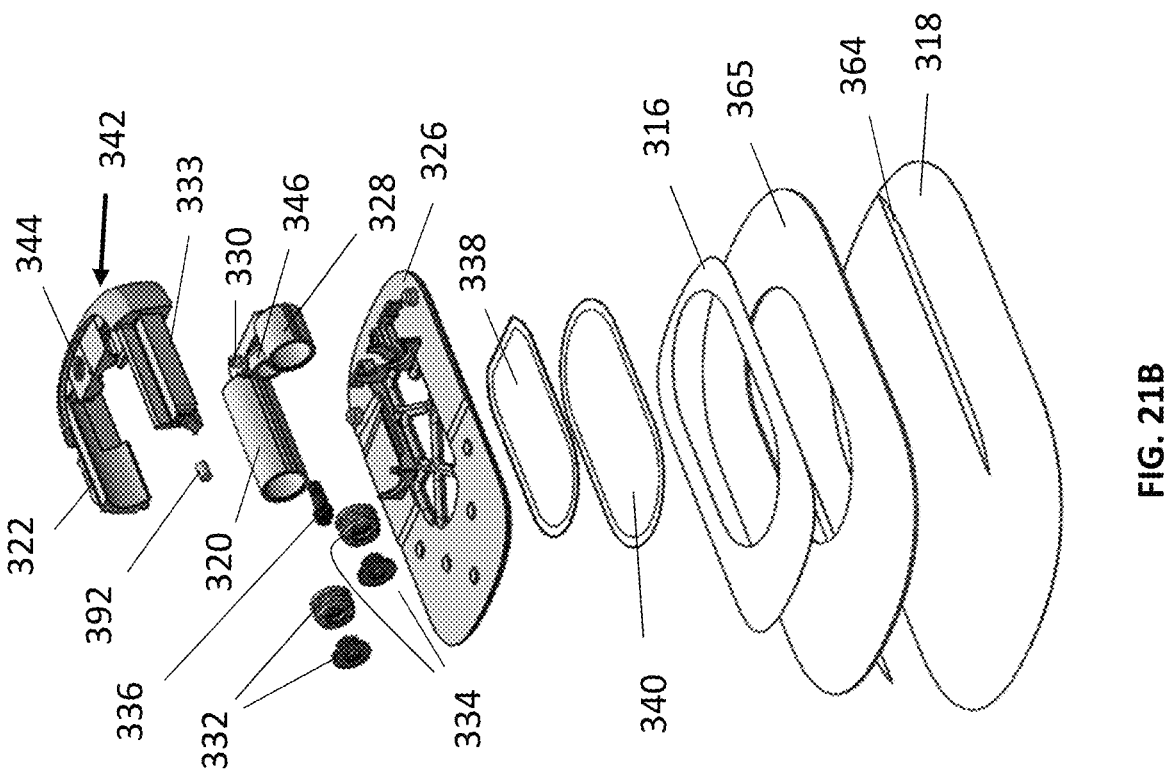
FIG. 21B is an exploded view of the disposable part of FIG. 21A.
Figure 21A:
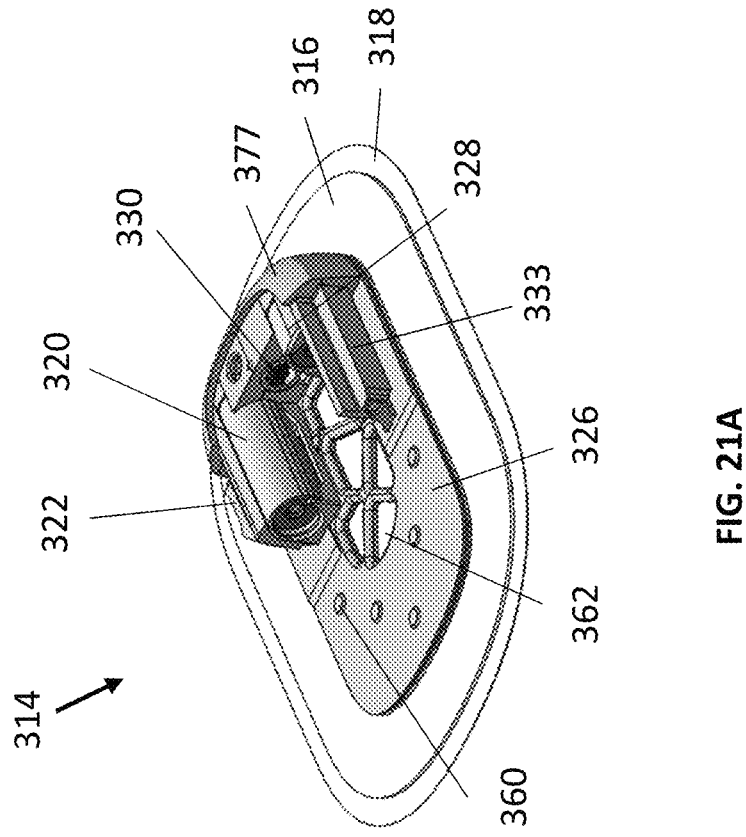
FIG. 21A is another perspective view of the disposable part of the two-part bioactive delivery system of FIG. 9.
Figure 21C:
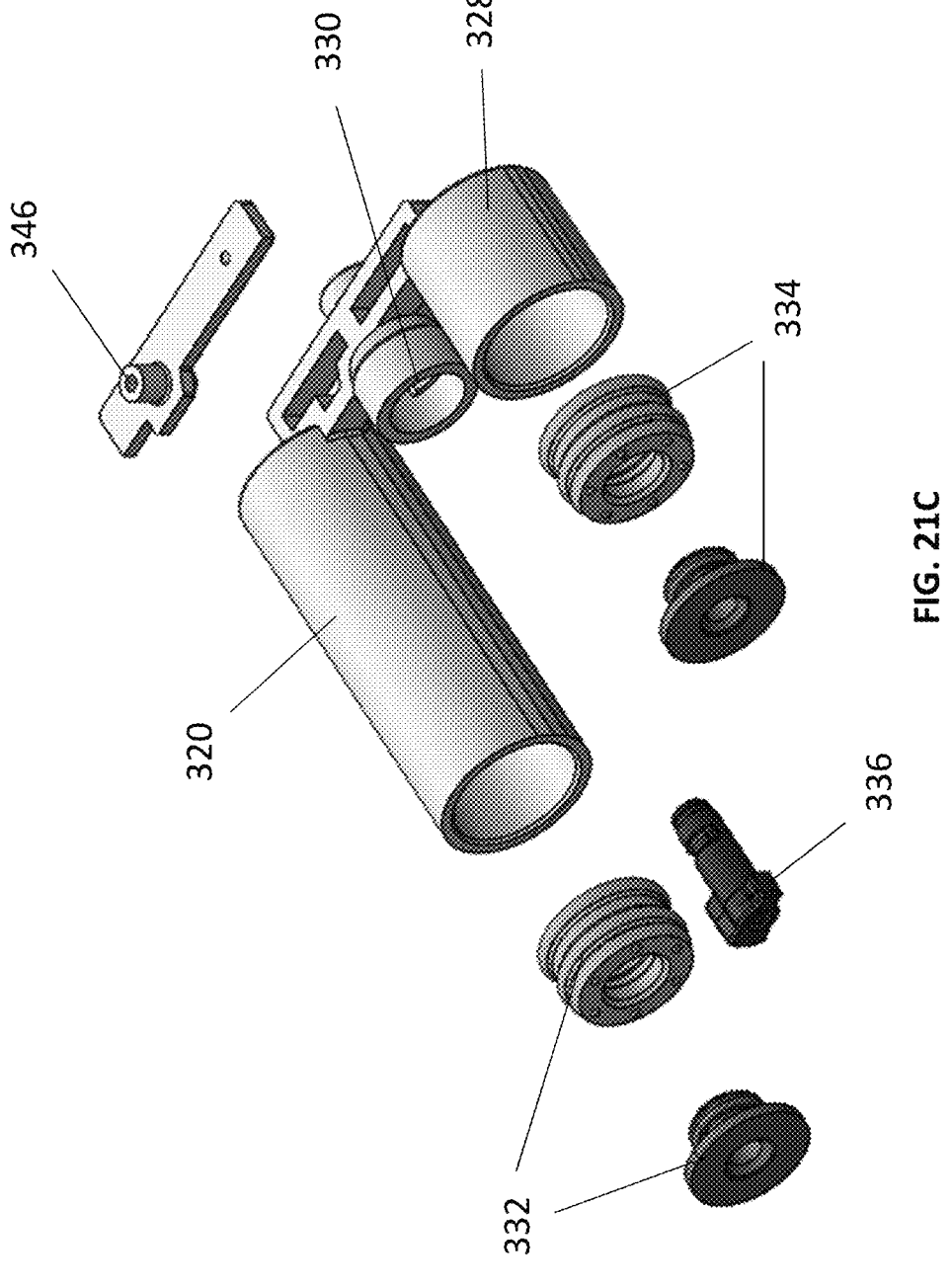
FIG. 21C is an exploded view of the fluidics assembly of FIGS. 21A and 21B.
Figure 22:
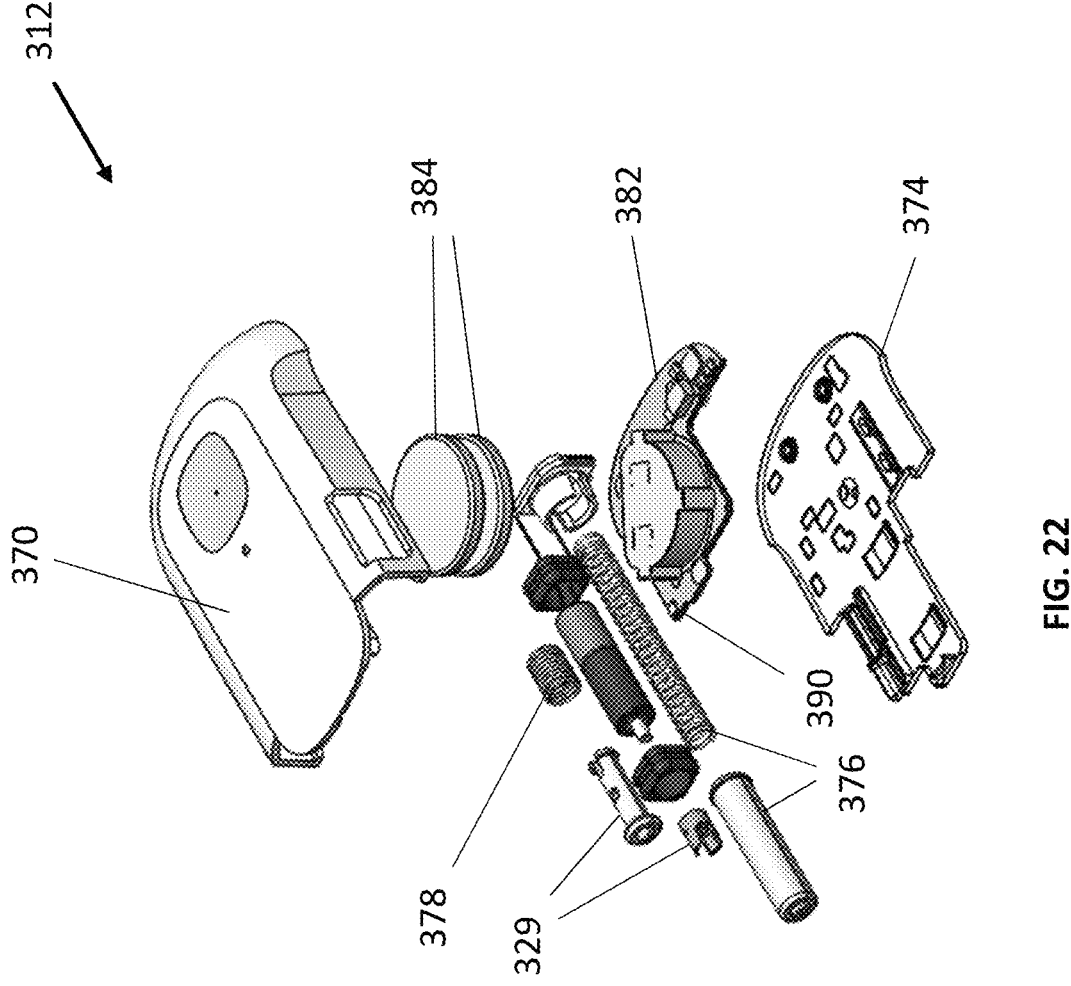
FIG. 22 is an exploded view of the reusable part of the two-part bioactive agent delivery system of FIG. 9.

Further details of the disposable part 314 are shown in FIGS. 21A-21C, and further details of the reusable part 312 are shown in FIG. 22. The disposable part 314 can further include a transdermal delivery patch 340, a permeable membrane 338 and a foam adhesive 365 with deadening strips 364. The deadening strips 364 can provide the user with an edge or small flap to grab onto to help remove the system 310 from the skin. An opening 344 in housing 342 leads to a fill port 346 that can be used to add a solution of the bioactive agent to reservoir 320 and bolus chamber 328. Movable pistons 332 and 334 are disposed within the reservoir 320 and bolus chamber 328, respectively. The reusable part 312 can include a printed circuit board 382 positioned over the lower housing 374, bolus spring assembly 378 (to control piston 334), reservoir spring assembly 376 (to control piston 332). A motor 329 can control activation of the valve 336 and spring assemblies 376, 378. A power supply 384 (e.g., batteries) can provide power to the motor 329. A detect magnet 392 can be positioned in the disposable part 314 while a magnetoresistive switch 390 can be positioned on the printed circuit board 382 of the reusable part 312 to detect attachment of the disposable part 314 to the reusable part 312 (i.e., when the magnet 392 and switch 390 are adjacent to one another upon attachment of the reusable part 312 and the disposable part 314).

The system 310 can operate similar to system 10. The disposable part 314 may be connected to the reusable part 312 by sliding the rail 333 and sliding element 382 relative to one another until the components are latched with latch components 322 and 386. This connection compresses spring assemblies 376 and 378 against pistons 332 and 334 of reservoir 320 and bolus chamber 328, respectively, to pressurize the bioactive agent solution in the reservoir 320 and bolus chamber 328. In response to a signal from the device's microprocessor, motor assembly 380 turns rotatable valve element 336 to a position in which the contents of bolus chamber 328 are delivered to the patient's skin through the transdermal delivery patch 340. As the bioactive agent moves onto the user's skin, solvent from the bioactive agent solution evaporates through the gas permeable membrane 338 and the vents 362 in chassis 326 to reach the flow path defined by gap 364. Further details of the operation of the reusable and disposable parts and components to deliver the bioactive agent solution to the transdermal patch at controlled times may be found in US Publication No. 2016/0220798, the disclosure of which is incorporated by reference.

It should be understood that any element described herein with respect to one embodiment can be added to or substituted for any element described with respect to another embodiment.

When a feature or element is herein referred to as being "on" another feature or element, it can be directly on the other feature or element or intervening features and/or elements may also be present. In contrast, when a feature or element is referred to as being "directly on" another feature or element, there are no intervening features or elements present. It will also be understood that, when a feature or element is referred to as being "connected", "attached" or "coupled" to another feature or element, it can be directly connected, attached or coupled to the other feature or element or intervening features or elements may be present. In contrast, when a feature or element is referred to as being "directly connected", "directly attached" or "directly coupled" to another feature or element, there are no intervening features or elements present. Although described or shown with respect to one embodiment, the features and elements so described or shown can apply to other embodiments. It will also be appreciated by those of skill in the art that references to a structure or feature that is disposed "adjacent" another feature may have portions that overlap or underlie the adjacent feature.

Terminology used herein is for the purpose of describing particular embodiments only and is not intended to be limiting of the invention. For example, as used herein, the singular forms "a", "an" and "the" are intended to include the plural forms as well, unless the context clearly indicates otherwise. It will be further understood that the terms "comprises" and/or "comprising," when used in this specification, specify the presence of stated features, steps, operations, elements, and/or components, but do not preclude the presence or addition of one or more other features, steps, operations, elements, components, and/or groups thereof. As used herein, the term "and/or" includes any and all combinations of one or more of the associated listed items and may be abbreviated as "/".

Spatially relative terms, such as "under", "below", "lower", "over", "upper" and the like, may be used herein for case of description to describe one element or feature's relationship to another element(s) or feature(s) as illustrated in the figures. It will be understood that the spatially relative terms are intended to encompass different orientations of the device in use or operation in addition to the orientation depicted in the figures. For example, if a device in the figures is inverted, elements described as "under" or "beneath" other elements or features would then be oriented "over" the other elements or features. Thus, the exemplary term "under" can encompass both an orientation of over and under. The device may be otherwise oriented (rotated 90 degrees or at other orientations) and the spatially relative descriptors used herein interpreted accordingly. Similarly, the terms "upwardly", "downwardly", "vertical", "horizontal" and the like are used herein for the purpose of explanation only unless specifically indicated otherwise.

Although the terms "first" and "second" may be used herein to describe various features/elements (including steps), these features/elements should not be limited by these terms, unless the context indicates otherwise. These terms may be used to distinguish one feature/element from another feature/element. Thus, a first feature/element discussed below could be termed a second feature/element, and similarly, a second feature/element discussed below could be termed a first feature/element without departing from the teachings of the present invention.

Throughout this specification and the claims which follow, unless the context requires otherwise, the word "comprise", and variations such as "comprises" and "comprising" means various components can be co-jointly employed in the methods and articles (e.g., compositions and apparatuses including device and methods). For example, the term "comprising" will be understood to imply the inclusion of any stated elements or steps but not the exclusion of any other elements or steps.

As used herein in the specification and claims, including as used in the examples and unless otherwise expressly specified, all numbers may be read as if prefaced by the word "about" or "approximately," even if the term does not expressly appear. The phrase "about" or "approximately" may be used when describing magnitude and/or position to indicate that the value and/or position described is within a reasonable expected range of values and/or positions. For example, a numeric value may have a value that is +/−0.1% of the stated value (or range of values), +/−1% of the stated value (or range of values), +/−2% of the stated value (or range of values), +/−5% of the stated value (or range of values), +/−10% of the stated value (or range of values), etc. Any numerical values given herein should also be understood to include about or approximately that value, unless the context indicates otherwise. For example, if the value "10" is disclosed, then "about 10" is also disclosed. Any numerical range recited herein is intended to include all sub-ranges subsumed therein. It is also understood that when a value is disclosed that "less than or equal to" the value, "greater than or equal to the value" and possible ranges between values are also disclosed, as appropriately understood by the skilled artisan. For example, if the value "X" is disclosed the "less than or equal to X" as well as "greater than or equal to X" (e.g., where X is a numerical value) is also disclosed. It is also understood that the throughout the application, data is provided in a number of different formats, and that this data, represents endpoints and starting points, and ranges for any combination of the data points. For example, if a particular data point "10" and a particular data point "15" are disclosed, it is understood that greater than, greater than or equal to, less than, less than or equal to, and equal to 10 and 15 are considered disclosed as well as between 10 and 15. It is also understood that each unit between two particular units are also disclosed. For example, if 10 and 15 are disclosed, then 11, 12, 13, and 14 are also disclosed.

Although various illustrative embodiments are described above, any of a number of changes may be made to various embodiments without departing from the scope of the invention as described by the claims. For example, the order in which various described method steps are performed may often be changed in alternative embodiments, and in other alternative embodiments one or more method steps may be skipped altogether. Optional features of various device and system embodiments may be included in some embodiments and not in others. Therefore, the foregoing description is provided primarily for exemplary purposes and should not be interpreted to limit the scope of the invention as it is set forth in the claims.

The examples and illustrations included herein show, by way of illustration and not of limitation, specific embodiments in which the subject matter may be practiced. As mentioned, other embodiments may be utilized and derived there from, such that structural and logical substitutions and changes may be made without departing from the scope of this disclosure. Such embodiments of the inventive subject matter may be referred to herein individually or collectively by the term "invention" merely for convenience and without intending to voluntarily limit the scope of this application to any single invention or inventive concept, if more than one is, in fact, disclosed. Thus, although specific embodiments have been illustrated and described herein, any arrangement calculated to achieve the same purpose may be substituted for the specific embodiments shown. This disclosure is intended to cover any and all adaptations or variations of various embodiments. Combinations of the above embodiments, and other embodiments not specifically described herein, will be apparent to those of skill in the art upon reviewing the above description.

What is claimed is:

1. A two-part bioactive agent delivery system, the system comprising:

a disposable part comprising
an agent reservoir,
a transdermal patch communicating with the agent reservoir and adapted to transdermally deliver the bioactive agent to a user, the transdermal patch having a bottom surface adapted to contact skin of the user and a top surface opposite the bottom surface;
a rail configured to extend substantially parallel with a longitudinal axis of the two-part bioactive agent delivery system; and
a gas permeable membrane disposed over the top surface of the transdermal patch;
a reusable part comprising:
a power source and control electronics, the control electronics being adapted to deliver bioactive agent dissolved in a solvent from the agent reservoir to the transdermal patch;
a sliding element configured to engage with the rail of the disposable part and form a gap between the reusable part and the disposable part; and
a solvent removal element disposed in the gap between the disposable part and the reusable part to create a flow path for gaseous solvent to flow from the gas permeable membrane to ambient air around the bioactive agent delivery system; and
a vent positioned between the gas permeable membrane and the gap, wherein the vent is configured to expose between 5-30% of a surface of the gas permeable membrane.

2. The system of claim 1, wherein the reusable part further comprises one or more spacers configured to engage with the disposable part and maintain the gap between the reusable part and the disposable part.

3. The system of claim 2, wherein the one or more spacers are further configured to engage with a bottom surface of the reusable part to maintain the gap between the reusable part and the disposable part.

4. The system of claim 2, wherein the one or more spacers are substantially equally disposed around the vent.

5. The system of claim 1, wherein the disposable part further comprises a chassis configured to include the agent reservoir and the rail.

6. The system of claim 5, further comprising spacers configured to include a diameter of less than ten percent of a width of the chassis.

7. The system of claim 5, wherein the chassis includes a thicker section and a thinner section, wherein the thinner section partly defines the gap.

8. The system of claim 7, wherein the chassis further includes a ramp ledge configured to transition between the thicker section and the thinner section.

9. The system of claim 1, further comprising a diagonal strut configured to divide the vent into a plurality of vents.

10. The system of claim 1, wherein the disposable part comprises the vent.

11. The system of claim 1, further comprising at least one drainage port formed in an exterior surface of the reusable part or the disposable part.

12. The system of claim 1, wherein the disposable part further comprises an agent outlet communicating with the agent reservoir and the transdermal patch.

13. The system of claim 12, wherein the agent outlet is configured to provide the bioactive agent dissolved in the solvent to a space between the transdermal patch and the gas permeable membrane.

14. A method of delivering a bioactive agent, the method comprising:

connecting a sliding element of a reusable part of a delivery system to a rail of a disposable part of the delivery system to form a flow path within a gap between the reusable part and the disposable part;

delivering the bioactive agent dissolved in a solvent from a reservoir of the disposable part to a transdermal membrane of the disposable part; and allowing the solvent to evaporate and flow from the transdermal membrane through a gas permeable membrane and a vent disposed over the gas permeable membrane to the gap and along the flow path to ambient air around the delivery system, wherein the vent exposes between 5-30% of a surface of the gas permeable membrane.

15. The method of claim 14, wherein delivering the bioactive agent comprises controlling, with the reusable part, movement of the bioactive agent dissolved in the solvent from the reservoir to the transdermal membrane.

16. The method of claim 15, wherein controlling movement of the bioactive agent comprises actuating a valve.

17. The method of claim 15, further comprising detecting a connection between the disposable part and the reusable part.

18. The method of claim 17, wherein detecting a connection comprises sensing a magnetic field.

19. A two-part bioactive agent delivery system, the system comprising:

a disposable part comprising
an agent reservoir,
a transdermal patch communicating with the agent reservoir and adapted to transdermally deliver the bioactive agent to a user, the transdermal patch having a bottom surface adapted to contact skin of the user and a top surface opposite the bottom surface;
a rail configured to extend substantially parallel with a longitudinal axis of the two-part bioactive agent delivery system; and
a gas permeable membrane disposed over the top surface of the transdermal patch;

a reusable part comprising:
a power source and control electronics, the control electronics being adapted to deliver bioactive agent dissolved in a solvent from the agent reservoir to the transdermal patch;
a sliding element configured to engage with the rail of the disposable part and form a gap between the reusable part and the disposable part; and a solvent removal element comprising a gap disposed between the disposable part and the reusable part to create a flow path for gaseous solvent to flow from the gas permeable membrane to ambient air around the bioactive agent delivery system; and a vent configured to expose between 5-30% of a surface of the gas permeable membrane to the gap.

* * * * *